United States Patent
Nairne et al.

(10) Patent No.: US 8,431,111 B2
(45) Date of Patent: *Apr. 30, 2013

(54) PEPTIDE IMAGING AGENTS

(75) Inventors: Robert James Domett Nairne, Amersham (GB); Andrew John Healey, Oslo (NO); Edvin Wilhelm Johannesen, Oslo (NO)

(73) Assignee: GE Healthcare Limited, Amersham (GB)

( * ) Notice: Subject to any disclaimer, the term of this patent is extended or adjusted under 35 U.S.C. 154(b) by 316 days.

This patent is subject to a terminal disclaimer.

(21) Appl. No.: 12/671,076

(22) PCT Filed: Jul. 29, 2008

(86) PCT No.: PCT/EP2008/059941
§ 371 (c)(1),
(2), (4) Date: Mar. 23, 2010

(87) PCT Pub. No.: WO2009/016180
PCT Pub. Date: Feb. 5, 2009

(65) Prior Publication Data
US 2010/0178253 A1    Jul. 15, 2010

Related U.S. Application Data

(60) Provisional application No. 60/976,818, filed on Oct. 2, 2007.

(30) Foreign Application Priority Data

Jul. 31, 2007 (WO) ................ PCT/GB2007/002907
Sep. 28, 2007 (GB) .................................. 0718967.3

(51) Int. Cl.
*A61B 5/00* (2006.01)
*A61B 8/00* (2006.01)

(52) U.S. Cl.
USPC ......... 424/9.6; 424/1.11; 424/1.65; 424/1.69; 424/9.1; 530/317; 530/324; 530/325; 530/326

(58) Field of Classification Search ................ 424/1.11, 424/1.65, 1.69, 9.1, 9.2, 9.6; 514/1, 1.11; 530/300, 317, 323, 325, 326, 332–345; 540/1; 548/100, 146, 215, 300.1, 400; 549/200
See application file for complete search history.

(56) References Cited

U.S. PATENT DOCUMENTS

| | | |
|---|---|---|
| 2002/0115862 A1 | 8/2002 | Czerney et al. |
| 2004/0110161 A1 | 6/2004 | Kappel et al. |
| 2004/0162423 A1 | 8/2004 | Czerney et al. |

FOREIGN PATENT DOCUMENTS

| | | |
|---|---|---|
| EP | 1674478 | 6/2006 |
| WO | 01/90253 | 11/2001 |
| WO | 2004/078778 | 9/2004 |
| WO | 2005/030266 | 4/2005 |
| WO | 2008/015415 | 2/2008 |
| WO | 2008/139207 | 11/2008 |
| WO | 2009/026177 | 2/2009 |

OTHER PUBLICATIONS

M-R Lisy, et.al. "Diagnosis of Peritonitis Using Near-Infrared Optical Imaging of In Vivo Labeled Monocytes-Macrophages" Journal of Biomedical Optics, vol. 11, No. 6, Jan. 2, 2007 pp. 064014-1 to 064014-9.
Towner, et.al. "In Vivo Molecular Magnetic Resonance.." Proc. Am. Assoc. Cancer Research Ann. Mtg. (2006), Vol. 47, p. 237.
PCT/EP2008/059941 ISRWO Dated Dec. 10, 2009.
GB0718967.3 Search Report Dated Jan. 28, 2008.

*Primary Examiner* — D L Jones
(74) *Attorney, Agent, or Firm* — Yonggang Ji

(57) ABSTRACT

The present invention relates to labelled cMet binding peptides suitable for optical imaging in vivo. The peptides are labelled with a benzopyrylium dye suitable for imaging in the red to near-infrared region. Also disclosed are pharmaceutical compositions and kits, as well as in vivo imaging methods, especially of use in the detection, staging, diagnosis, monitoring of disease progression or monitoring of treatment of colorectal cancer (CRC).

29 Claims, No Drawings

PEPTIDE IMAGING AGENTS

This application is a filing under 35 U.S.C. 371 of international application number PCT/EP2008/059941, filed Jul. 29, 2008, which claims priority to international application number PCT/GB2007/002907 filed Jul. 31, 2007 in Great Britain, and application number 0718967.3 filed Sep. 28, 2007 in Great Britain, and application number 60/976,818 filed Oct. 2, 2007 in the U.S., the entire disclosure of each of which is hereby incorporated by reference.

FIELD OF THE INVENTION

The present invention relates to labelled cMet binding peptides suitable for optical imaging in vivo. The peptides are labelled with an optical reporter group suitable for imaging in the red to near-infrared region. Also disclosed are in vivo imaging methods, especially of use in the diagnosis of colorectal cancer (CRC).

BACKGROUND TO THE INVENTION

WO 2005/030266 discloses that there is a medical need for early diagnosis of colorectal cancer (CRC). WO 2005/030266 discloses optical imaging contrast agents which have affinity for a biological target abnormally expressed in CRC. The biological target is selected from: COX-2, beta-catenin, E-cadherin, P-cadherin, various kinases, Her-2, matrix metalloproteinases (MMPs), cyclins, P53, thymidylate synthase, VEGF receptors, EGF receptors, K-ras, adenomatous polyposis coli protein, cathepsin B, uPAR, cMet, mucins and gastrin receptors. Preferred such targets (p. 7 lines 11-12) are said to be: cMet, MMP-14, COX-2, beta-catenin and Cathepsin B. The vector of WO 2005/030266 can be: a peptide, peptoid moiety, oligonucleotide, oligosaccharide, lipid-related compound or traditional organic drug-like small molecule. The reporter moiety is preferably a dye that interacts with light in the wavelength region from the ultraviolet to the infrared part of the electromagnetic spectrum.

Hepatocyte growth factor (HGF), also known as scatter factor (SF), is a growth factor which is involved in various physiological processes, such as wound healing and angiogenesis. The HGF interaction with its high affinity receptor (cMet) is implicated in tumour growth, invasion and metastasis.

Knudsen et al have reviewed the role of HGF and cMet in prostate cancer, with possible implications for imaging and therapy [Adv. Cancer Res., 91, 31-67 (2004)]. Labelled anti-met antibodies for diagnosis and therapy are described in WO 03/057155.

WO 2004/078778 discloses polypeptides or multimeric peptide constructs which bind cMet or a complex comprising cMet and HGF. Approximately 10 different structural classes of peptide are described. WO 2004/078778 discloses that the peptides can be labelled with a detectable label for in vitro and in vivo applications, or with a drug for therapeutic applications. The detectable label can be: an enzyme, fluorescent compound, an optical dye, a paramagnetic metal ion, an ultrasound contrast agent or a radionuclide. Preferred labels of WO 2004/078778 are stated to be radioactive or paramagnetic, and most preferably comprise a metal which is chelated by a metal chelator.

THE PRESENT INVENTION

The present invention provides imaging agents suitable for in vivo optical imaging, which comprise cMet binding cyclic peptides, and a benzopyrylium dye suitable for imaging the mammalian body in vivo using light of red to near-infrared wavelength 600-1200 mm The cMet binding cyclic peptides are related to one of the structural classes of peptide of WO 2004/078778, and have optimal binding affinity for cMet. These peptides were derived from phage display and selected by their affinity for cMet and lack of competition with HGF, as described in WO 2004/078778. The cMet binding peptides of the present invention preferably have at least one of their termini protected by metabolism inhibiting groups ($M^{IG}$). That is an important consideration for in vivo applications, where endogenous enzymes and peptidases would otherwise rapidly metabolise the peptide, with consequent loss of cMet binding affinity, and hence loss of selective targeting in vivo.

The present invention teaches that the best way of using cMet binding peptides for in vivo imaging of superficial lesions involves the use of an optical reporter, as opposed to other imaging modalities (eg. nuclear, MRI or ultrasound), and also provides preferred optical imaging reporters. The red to near-infrared region (light of wavelength 600-1200 nm) is preferred, since that region has minimal spectral overlap with endogenous tissues and materials, such as haemoglobin, porphyrins, melanin, and collagen [Licha, Topics Curr. Chem., 222, 1-29 (2002)]. Other important contributors to tissue autofluorescence are NADH, FAD and elastin.

DETAILED DESCRIPTION OF THE INVENTION

In a first aspect, the present invention provides an imaging agent which comprises a conjugate of Formula I:

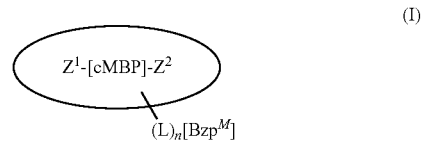

(I)

where:
$Z^1$ is attached to the N-terminus of cMBP, and is H or $M^{IG}$;
$Z^2$ is attached to the C-terminus of cMBP and is OH, $OB^c$, or $M^{IG}$,
where $B^C$ is a biocompatible cation;
cMBP is a cMet binding cyclic peptide of 17 to 30 amino acids which comprises the amino acid sequence (SEQ-1):

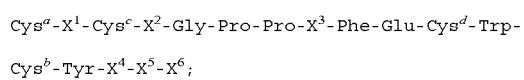

wherein $X^1$ is Asn, His or Tyr;
$X^2$ is Gly, Ser, Thr or Asn;
$X^3$ is Thr or Arg;
$X^4$ is Ala, Asp, Glu, Gly or Ser;
$X^5$ is Ser or Thr;
$X^6$ is Asp or Glu;
and $Cys^{a-d}$ are each cysteine residues such that residues a and b as well as c and d are cyclised to form two separate disulfide bonds;
$M^{IG}$ is a metabolism inhibiting group which is a biocompatible group which inhibits or suppresses in vivo metabolism of the peptide;
L is a synthetic linker group of formula $-(A)_m-$ wherein each A is independently $-CR_2-$, $-CR=CR-$, —C≡C—, —CR$_2$CO$_2$—, —CO$_2$CR$_2$—, —NRCO—, —CONR—, —NR(C=O)NR—, —NR(C=S)NR—, —SO$_2$NR—, —NRSO$_2$—, —CR$_2$OCR$_2$—, —CR$_2$SCR$_2$—, —CR$_2$NRCR$_2$—, a C$_{4-8}$ cycloheteroalkylene group, a C$_{4-8}$ cycloalkylene group, a C$_{5-12}$ arylene group, or a C$_{3-12}$ heteroarylene group, an amino acid, a sugar or a monodisperse polyethyleneglycol (PEG) building block;

each R is independently chosen from H, C$_{1-4}$ alkyl, C$_{2-4}$ alkenyl, C$_{2-4}$ alkynyl, C$_{1-4}$ alkoxyalkyl or C$_{1-4}$ hydroxyalkyl;

m is an integer of value 1 to 20;

n is an integer of value 0 or 1;

Bzp$^M$ is a benzopyrylium dye of Formula II:

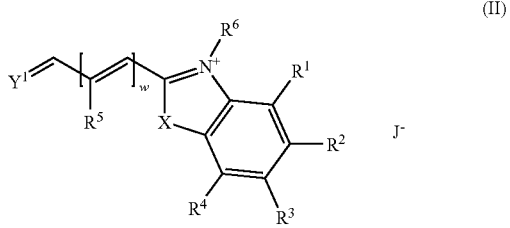

(II)

where:

Y$^1$ is a group of Formula Y$^a$ or Y$^b$

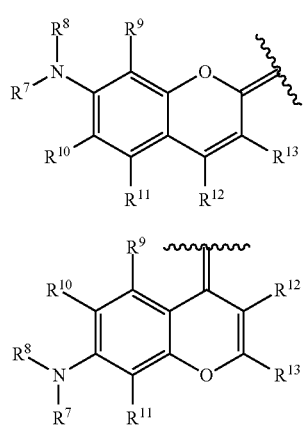

(Y$^a$)

(Y$^b$)

R$^1$-R$^4$ and R$^9$-R$^{13}$ are independently selected from H, —SO$_3$M$^1$, Hal, R$^a$ or C$_{3-12}$ aryl, where each M$^1$ is independently H or B$^c$, and B$^c$ is a biocompatible cation;

R$^5$ is H, C$_{1-4}$ alkyl, C$_{1-6}$ carboxyalkyl, C$_{3-12}$ arylsulfonyl, Cl, or R$^5$ together with one of R$^6$, R$^{14}$, R$^{15}$ or R$^{16}$ may optionally form a 5- or 6-membered unsaturated aliphatic, unsaturated heteroaliphatic or aromatic ring;

R$^6$ and R$^{16}$ are independently R$^a$ groups;

R$^7$ and R$^8$ are independently C$_{1-4}$ alkyl, C$_{1-4}$ sulfoalkyl or C$_{1-6}$ hydroxyalkyl or optionally together with one or both of R$^9$ and/or R$^{10}$ may form a 5- or 6-membered N-containing heterocyclic or heteroaryl ring;

X is —CR$^{14}$R$^{15}$—, —O—, —S—, —Se—, —NR$^{16}$— or —CH=CH—, where R$^{14}$ to R$^{16}$ are independently R$^a$ groups;

R$^a$ is C$_{1-4}$ alkyl, C$_{1-4}$ sulfoalkyl, C$_{1-6}$ carboxyalkyl or C$_{1-6}$ hydroxyalkyl;

w is 1 or 2;

J is a biocompatible anion;

with the proviso that Bzp$^M$ comprises at least one sulfonic acid substituent chosen from the R$^1$ to R$^{16}$ groups.

By the term "imaging agent" is meant a compound suitable for imaging the mammalian body in vivo. Preferably, the mammal is a human subject. The imaging may be invasive (eg. intra-operative or endoscopy) or non-invasive. The preferred imaging method is endoscopy. Whilst the conjugate of Formula I is suitable for in vivo imaging, it may also have in vitro applications (eg. assays quantifying cMet in to biological samples or visualisation of cMet in tissue samples). Preferably, the imaging agent is used for in vivo optical imaging.

By the term "optical imaging" is meant any method that forms an image for detection, staging or diagnosis of disease, follow up of disease development or for follow up of disease treatment based on interaction with light in the red to near-infrared region (wavelength 600-1200 nm). Optical imaging further includes all methods from direct visualization without use of any device and involving use of devices such as various scopes, catheters and optical imaging equipment, eg. computer-assisted hardware for tomographic presentations. The modalities and measurement techniques include, but are not limited to: luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; interferometry; coherence interferometry; diffuse optical tomography and fluorescence mediated diffuse optical tomography (continuous wave, time domain and frequency domain systems), and measurement of light scattering, absorption, polarization, luminescence, fluorescence lifetime, quantum yield, and quenching. Further details of these techniques are provided by: (Tuan Vo-Dinh (editor): "Biomedical Photonics Handbook" (2003), CRC Press LCC; Mycek & Pogue (editors): "Handbook of Biomedical Fluorescence" (2003), Marcel Dekker, Inc.; Splinter & Hopper: "An Introduction to Biomedical Optics" (2007), CRC Press LCC.

The red to near-infrared region light is preferably of wavelength 650-1000 nm. The optical imaging method is preferably fluorescence endoscopy.

By the term "conjugate" is meant that the cMBP and Bzp$^M$ dye are linked by covalent bonds, optionally via the (L)$_n$ group.

The Z$^1$ group substitutes the amine group of the last amino acid residue. Thus, when Z$^1$ is H, the amino terminus of the cMBP terminates in a free NH$_2$ group of the last amino acid residue. The Z$^2$ group substitutes the carbonyl group of the last amino acid residue. Thus, when Z$^2$ is OH, the carboxy terminus of the cMBP terminates in the free CO$_2$H group of the last amino acid residue, and when Z$^2$ is OB$^c$ that terminal to carboxy group is ionised as a CO$_2$B$^c$ carboxylate group.

By the term "metabolism inhibiting group" (M$^{IG}$) is meant a biocompatible group which inhibits or suppresses in vivo metabolism of the cMBP peptide at either the amino terminus (Z$^1$) or carboxy terminus (Z$^2$). Such groups are well known to those skilled in the art and are suitably chosen from, for the peptide amine terminus: N-acylated groups —NH(C=O)R$^G$ where the acyl group —(C=O)R$^G$ has R$^G$ chosen from: C$_{1-6}$ alkyl, C$_{3-10}$ aryl groups or comprises a polyethyleneglycol (PEG) building block. Suitable PEG groups are described for the linker group (L), below. Preferred such PEG groups are the biomodifiers of Formula IA or IB. Preferred such amino terminus M$^{IG}$ groups are acetyl, benzyloxycarbonyl or trifluoroacetyl, most preferably acetyl.

Suitable metabolism inhibiting groups for the peptide carboxyl terminus include: carboxamide, tert-butyl ester, benzyl ester, cyclohexyl ester, amino alcohol or a polyethyleneglycol (PEG) building block. A suitable $M^{IG}$ group for the carboxy terminal amino acid residue of the cMBP peptide is where the terminal amine of the amino acid residue is N-alkylated with a $C_{1-4}$ alkyl group, preferably a methyl group. Preferred such $M^{IG}$ groups are carboxamide or PEG, most preferred such groups are carboxamide.

Formula I denotes that the $(L)_n[Bzp^M]$ moiety can be attached at either $Z^1$, $Z^2$ or cMBP. For $Z^1$ or $Z^2$, the $(L)_n[Bzp^M]$ moiety may either be attached to the $M^{IG}$ group when either of $Z^1/Z^2$ is a $M^{IG}$. When $Z^1$ is H or $Z^2$ is OH, attachment of the $(L)_n[Bzp^M]$ moiety at the $Z^1$ or $Z^2$ position gives compounds of formulae $[Bzp^M]$-$(L)_n$-[cMBP]-$Z^2$ or $Z^1$-[cMBP]-$(L)_n$-$[Bzp^M]$ respectively. Inhibition of metabolism of the cMBP at either peptide terminus may also be achieved by attachment of the $(L)_n[Bzp^M]$ moiety in this way, but $(L)_n[Bzp^M]$ is outside the definition of $M^{IG}$ of the present invention.

The $-(L)_n-$ moiety of Formula I may be attached at any suitable position of the $Bzp^M$ of Formula II. The $(L)_n-$ moiety either takes the place of an existing substituent (eg. one of the $R^1$ to $R^{16}$ groups), or is covalently attached to the existing substituent of the $Bzp^M$. The $-(L)_n-$ moiety of Formula I is preferably attached via a carboxyalkyl substituent of the $Bzp^M$.

By the term "cMet binding cyclic peptide" (cMBP) is meant a peptide which binds to the hepatocyte growth factor (HGF) high affinity receptor, also known as cMet (c-Met, Met, Met receptor or hepatocyte growth factor receptor). Suitable cMBP peptides of the present invention have an apparent $K_d$ for cMet of cMet/HGF complex of less than about 20 nM. The cMBP peptides comprise proline residues, and it is known that such residues can exhibit cis/trans isomerisation of the backbone amide bond. The cMBP peptides of the present invention include any such isomers.

By the term "biocompatible cation" ($B^c$) is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium. By the term "biocompatible anion" (J) is meant a negatively charged counterion which forms a salt with an ionised, positively charged group (in this case an indolinium group), where said negatively charged counterion is also non-toxic and hence suitable for administration to the mammalian body, especially the human body. The counterion (J⁻) represents an anion which is present in a molar equivalent amount, this balancing the positive charge on the $Bzp^M$ dye. The anion (J) is suitably singly- or multiply-charged, as long as a charge-balancing amount is present. The anion is suitably derived from an inorganic or organic acid. Examples of suitable anions include: halide ions such as chloride or bromide; sulfate; nitrate; citrate; acetate; phosphate and borate. A preferred anion is chloride.

By the term "amino acid" is meant an L- or D-amino acid, amino acid analogue (eg. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids are used herein. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)].

By the term "peptide" is meant a compound comprising two or more amino acids, as defined above, linked by a peptide bond (ie. an amide bond linking the amine of one amino acid to the carboxyl of another). The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids.

Suitable imaging agents of the invention are those wherein the $Bzp^M$ is of Formula IIa or IIb:

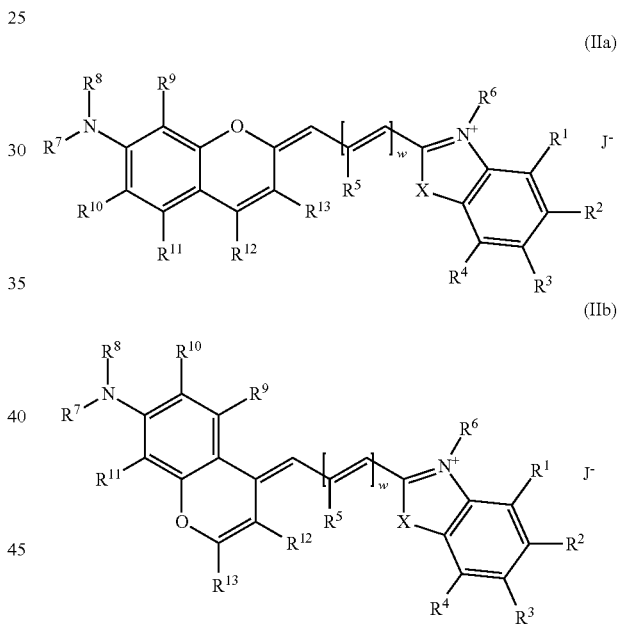

where X, w and $R^1$-$R^{13}$ and J are as defined for Formula II.

When $R^5$ together with one of $R^6/R^{14}$-$R^{16}$ forms a 5- or 6-membered unsaturated aliphatic, unsaturated heteroaliphatic or aromatic ring, suitable such aromatic rings include: phenyl, furan, thiazole, pyridyl, pyrrole or pyrazole rings. Suitable unsaturated rings comprise at least the C=C to which $R^5$ is attached.

When $R^7$ and/or $R^8$ together with one or both of $R^9$ and/or $R^{10}$ form a 5- or 6-membered N-containing heterocyclic or heteroaryl ring, suitable such rings include: thiazole, pyridyl, pyrrole or pyrazole rings or partially hydrogenated versions thereof. preferably pyridyl or dihydropyridyl.

By the term "sulfonic acid substituent" is meant a substituent of formula —$SO_3M^1$, where $M^1$ is H or $B^c$, and $B^c$ is a biocompatible cation (as defined above). The $SO_3M^1$, substituent is covalently bonded to a carbon atom, and the carbon atom may be aryl (ie. sulfoaryl such as when $R^1$ or $R^2$ is —$SO_3M^1$), or alkyl (ie. a sulfoalkyl group).

It is envisaged that one of the roles of the linker group $(A)_m$- of Formula I is to distance $Bzp^M$ from the binding site of the cMBP peptide, to minimise any steric impairment of interaction with the binding site. This can be achieved by a combination of flexibility (eg. simple alkyl chains), so that the bulky group has the freedom to position itself away from the active site and/or rigidity such as a cycloalkyl or aryl spacer which orientate the $Bzp^M$ away from the binding site. The nature of the linker group can also be used to modify the biodistribution of the imaging agent. Thus, eg. the introduction of ether groups in the linker will help to minimise plasma protein binding. When $-(A)_m$- comprises a polyethyleneglycol (PEG) building block or a peptide chain of 1 to 10 amino acid residues, the linker group may function to modify the pharmacokinetics and blood clearance rates of the imaging agent in vivo. Such "biomodifier" linker groups may accelerate the clearance of the imaging agent from background tissue, such as muscle or liver, and/or from the blood, thus giving a better diagnostic image due to less background interference. A biomodifier linker group may also be used to favour a particular route of excretion, eg. via the kidneys as opposed to via the liver.

By the term "sugar" is meant a mono-, di- or tri-saccharide. Suitable sugars include: glucose, galactose, maltose, mannose, and lactose. Optionally, the sugar may be functionalised to permit facile coupling to amino acids. Thus, eg. a glucosamine derivative of an amino acid can be conjugated to other amino acids via peptide bonds. The glucosamine derivative of asparagine (commercially available from NovaBiochem) is one example of this:

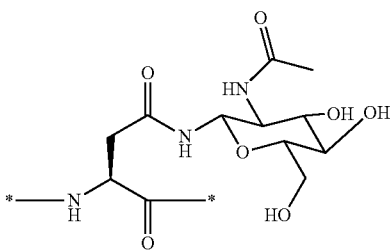 [SMILES: *N[C@@H](CC(=O)NC1OC(CO)C(O)C(O)C1NC(C)=O)C(*)=O]

Preferred Features

The molecular weight of the imaging agent is suitably up to 8000 Daltons. Preferably, the molecular weight is in the range 2800 to 6000 Daltons, most preferably 3000 to 4500 Daltons, with 3200 to 4000 Daltons being especially preferred.

Preferred imaging agents of the present invention have both peptide termini protected by $M^{IG}$ groups, ie. preferably both $Z^1$ and $Z^2$ are $M^{IG}$, which will usually be different. As noted above, either of $Z^1/Z^2$ may optionally represent $-(L)_n[Bzp^M]$. Having both peptide termini protected in this way is important for in vivo imaging applications, since otherwise rapid metabolism would be expected with consequent loss of selective binding affinity for cMet. When both $Z^1$ and $Z^2$ are $M^{IG}$, preferably $Z^1$ is acetyl and $Z^2$ is a primary amide. Most preferably, $Z^1$ is acetyl and $Z^2$ is a primary amide and the $(L)_n[Bzp^M]$ moiety is attached to the epsilon amine side chain of a lysine residue of cMBP.

Preferred cMBP peptides of the present invention have a $K_d$ for binding to cMet of less than about 10 nM (based on fluorescence polarisation assay measurements), most preferably less than 5 nM, with less than 3 nM being the ideal.

The peptide sequence (SEQ-1)

$Cys^a-X^1-Cys^c-X^2-Gly-Pro-Pro-X^3-Phe-Glu-Cys^d-Trp-Cys^b-Tyr-X^4-X^5-X^6$ of the cMBP of Formula I is a 17-mer peptide sequence, which is primarily responsible for the selective binding to cMet. When the cMBP peptide of the present invention comprises more than 17 amino acid residues, the remaining amino acids can be any amino acid apart from cysteine. Additional, unprotected cysteine residues could cause unwanted scrambling of the defined $Cys^a-Cys^b$ and $Cys^c-Cys^d$ disulfide bridges. The additional peptides preferably comprise at least one amino acid residue with a side chain suitable for facile conjugation of the $-(L)_n[Bzp^M]$ moiety. Suitable such residues include Asp or Glu residues for conjugation with amine-functionalised $-(L)_nBzp^M$ groups, or a Lys residue for conjugation with an amine-functionalised $-(L)_nBzp_M$ group. The amino acid residues for conjugation of $-(L)_n[Bzp^M]$ are suitably located away from the 17-mer binding region of the cMBP peptide (SEQ-1), and are preferably located at the C- or N-terminus. Preferably, the amino acid residue for conjugation is a Lys residue.

Substitution of the tryptophan residue of SEQ-1 was evaluated with the known amino acid substitutes phenylalanine and napthylalanine. Loss of cMet affinity was, however, found suggesting that the tryptophan residue is important for activity.

It is preferred that the cMBP peptide further comprises a N-terminal serine residue, giving the 18-mer (SEQ-2):

$Ser-Cys^a-X^1-Cys^c-X^2-Gly-Pro-Pro-X^3-Phe-Glu-Cys^d-Trp-Cys^b-Tyr-X^4-X^5-X^6$.

In addition to SEQ-1, or preferably SEQ-2, the cMBP most preferably further comprises either:
  (i) an Asp or Glu residue within 4 amino acid residues of either the C- or N-peptide terminus, and $(L)_nBzp^M$ is functionalised with an amine group which is conjugated to the carboxyl side chain of said Asp or Glu residue to give an amide bond;
  (ii) a Lys residue within 4 amino acid residues of either the C- or N-peptide terminus, and $(L)_nBzp^M$ is functionalised with a carboxyl group which is conjugated to the epsilon amine side chain of said Lys residue to give an amide bond.

Preferred cMBP peptides comprise the 22-mer amino acid sequence (SEQ-3):

$Ala-Gly-Ser-Cys^a-X^1-Cys^c-X^2-Gly-Pro-Pro-X^3-Phe-Glu-Cys^d-Trp-Cys^b-Tyr-X^4-X^5-X^6-Gly-Thr$.

The cMBP peptides of the present invention preferably have $X^3$ equal to Arg.

The cMBP peptide preferably further comprises in addition to SEQ-1, SEQ-2 or SEQ-3, at either the N- or C-terminus a linker peptide which is chosen from:

| | |
|---|---|
| -Gly-Gly-Gly-Lys-, | (SEQ-4) |
| -Gly-Ser-Gly-Lys- or | (SEQ-5) |
| -Gly-Ser-Gly-Ser-Lys-. | (SEQ-6) |

The Lys residue of the linker peptide is a most preferred location for conjugation of the -(L)$_n$[Bzp$^M$] moiety. Especially preferred cMBP peptides comprise SEQ-3 together with the linker peptide of SEQ-4, having the 26-mer amino acid sequence (SEQ-7):

Ala-Gly-Ser-Cys$^a$-Tyr-Cys$^c$-Ser-Gly-Pro-Pro-Arg-Phe-

Glu-Cys$^d$-Trp-Cys$^b$-Tyr-Glu-Thr-Glu-Gly-Thr-Gly-Gly-

Gly-Lys.

cMBP peptides of SEQ-1, SEQ-2, SEQ-3 and SEQ-7 preferably have $Z^1=Z^2=M^{IG}$, and most preferably have $Z^1$=acetyl and $Z^2$=primary amide.

The -(L)$_n$[Bzp$^M$] moiety is suitably attached to either of the $Z^1$ or $Z^2$ groups or an amino acid residue of the cMBP peptide which is different to the cMet binding sequence of SEQ-1. Preferred amino acid residues and sites of conjugation are as described above. When the -(L)$_n$[Bzp$^M$] moiety is attached to $Z^1$ or $Z^2$, it may take the place of $Z^1$ or $Z^2$ by conjugation to the N- or C-terminus, and block in vivo metabolism in that way.

The [Bzp$^M$]-(L)$_n$- moiety of Formula I is preferably attached at positions $R^5$, $R^6$, $R^{14}$, $R^{15}$ or $R^{16}$ of the Bzp$^M$ of Formula II, more preferably at $R^6$, $R^{14}$, $R^{15}$ or $R^{16}$ most preferably at $R^6$, $R^{14}$ or $R^{15}$. In order to facilitate the attachment, the relevant $R^5$, $R^6$, $R^{14}$, $R^{15}$ or $R^{16}$ substituent is preferably $C_{1-6}$ carboxyalkyl, more preferably $C_{3-6}$ carboxyalkyl.

The benzopyrylium dye (Bzp$^M$) preferably has at least 2 sulfonic acid substituents, more preferably 2 to 6 sulfonic acid substituents, most preferably 2 to 4 sulfonic acid substituents. Preferably, at least one of the sulfonic acid substituents is a $C_{1-4}$ sulfoalkyl group. Such sulfoalkyl groups are preferably located at positions $R^6$, $R^7$, $R^8$, $R^{14}$, $R^{15}$ or $R^{16}$; more preferably at $R^6$, $R^7$, $R^8$, $R^{14}$ or $R^{15}$; most preferably at $R^6$ together with one or both of $R^7$ and $R^8$ of Formula II. The sulfoalkyl groups of Formula II, are preferably of formula —(CH$_2$)$_k$SO$_3$M$^1$, where M$^1$ is H or B$^c$, k is an integer of value 1 to 4, and B$^c$ is a biocompatible cation (as defined above). k is preferably 3 or 4.

In Formula II, w is preferably 1. is preferably H or $C_{1-4}$ carboxyalkyl, and is most preferably H. X is preferably —CR$^{14}$R$^{15}$— or —NR$^{16}$—, and is most preferably —CR$^{14}$R$^{15}$—.

Preferred Bzp$^M$ dyes are of Formula III:

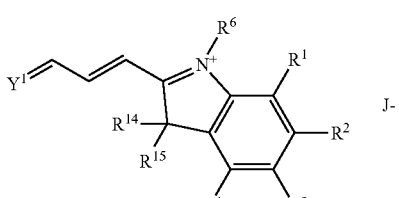

(III)

where Y$^1$, R$^1$-R$^4$, R$^6$, R$^{14}$, R$^{15}$ and J are as defined for Formula II. Suitable dyes of Formula III are of Formula IIIa or IIIb:

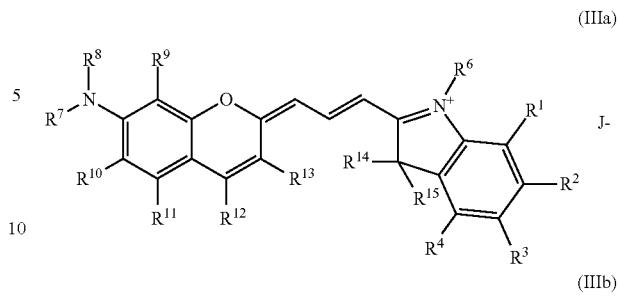

(IIIa)

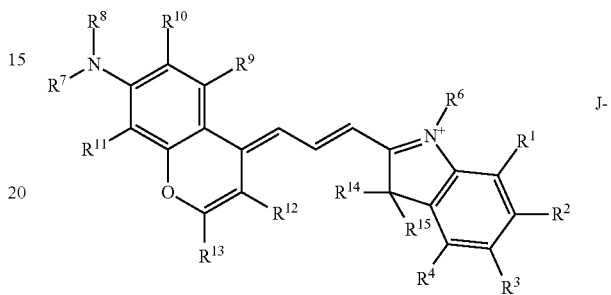

(IIIb)

Preferred R$^1$-R$^4$ and R$^6$-R$^{13}$ groups of Formulae III, IIIa and IIIb are as described above for Formulae IIa and IIb. In Formulae III, IIIa and IIIb, R$^{14}$ and R$^{15}$ are preferably chosen such that one is an R$^b$ group and the other is an R$^c$ group. R$^b$ is $C_{1-2}$ alkyl, most preferably methyl. R$^c$ is $C_{1-4}$ alkyl, $C_{1-6}$ carboxyalkyl or $C_{1-4}$ sulfoalkyl, preferably $C_{3-6}$ carboxyalkyl or —(CH$_2$)$_k$SO$_3$M$^1$ where k is chosen to be 3 or 4.

Preferably the dyes of Formula III have a $C_{1-6}$ carboxyalkyl substituent to permit facile covalent attachment to the cMBP.

In Formula II or III, when R$^7$ and/or R$^8$ together with one or both of R$^9$ and/or R$^{10}$ form a 5- or 6-membered N-containing heterocyclic or heteroaryl ring, preferred such rings are pyridyl or dihydropyridyl. A preferred such Y$^1$ group wherein an R$^8$ group has been cyclised with R$^{10}$ is of Formula Y$^c$:

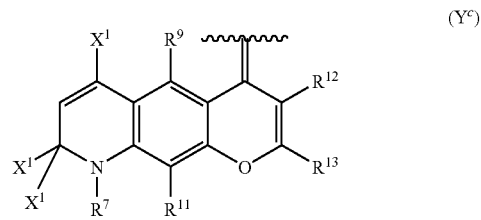

(Y$^c$)

A preferred such Y$^1$ group wherein both R$^7$ and R$^8$ group have been cyclised is of Formula Y$^d$:

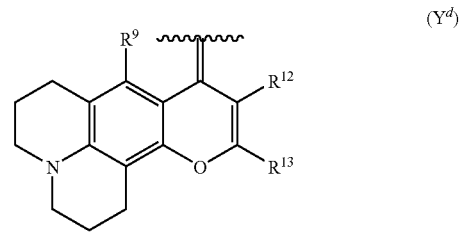

(Y$^d$)

where:
R$^7$, R$^9$ and R$^{11}$-R$^{13}$ are as defined above;
each E$^1$ is independently H or C$_{1-4}$ alkyl.
In Formula Y$^c$, it is preferred that:
each X$^1$ is CH$_3$;
R$^9$=R$^{11}$=H;
R$^{12}$ is H;
R$^{12}$ is CH$_3$ or C(CH$_3$)$_3$, more preferably —C(CH$_3$)$_3$.
In Formula Y$^d$, it is preferred that:
R=H;
R$^{12}$ is H;
R$^{12}$ is preferably CH$_3$ or C(CH$_3$)$_3$, more preferably —C(CH$_3$)$_3$.

It is preferred that the —NR$^7$R$^8$ group of Formula III is either:
(i) in open chain form, ie. the R$^7$/R$^8$ groups are not cyclised with one or both of R$^9$/R$^{10}$. Preferred such R$^7$ and R$^8$ groups are independently chosen from C$_{1-4}$ alkyl or C$_{1-4}$ sulfoalkyl, most preferably ethyl or C$_{3-4}$ sulfoalkyl;
(ii) cyclised to give a cyclic Y$^1$ substituent of Formula Y$^c$ or Y$^d$, more preferably of Formula Y$^c$.

The open chain form (i) is most preferred.
Especially preferred dyes of Formula III are of Formula IIIc, IIId or IIIe:

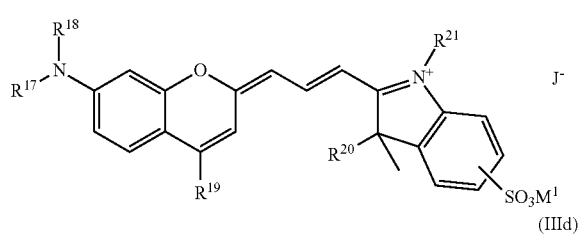

(IIIc)

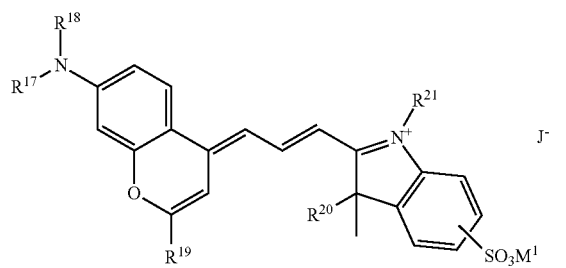

(IIId)

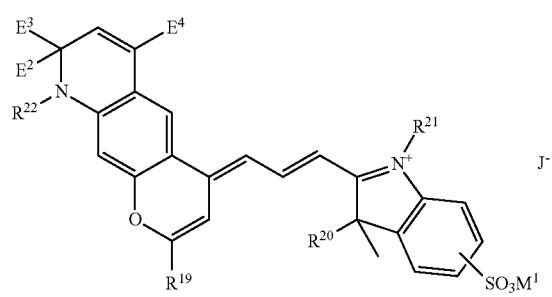

(IIIe)

where:
M$^1$ is as defined above;
R$^{17}$ and R$^{18}$ are independently chosen from C$_{1-4}$ alkyl or C$_{1-4}$ sulfoalkyl;
R$^{19}$ is H or C$_{1-4}$ alkyl;
R$^{20}$ is C$_{1-4}$ alkyl, C$_{1-4}$ sulfoalkyl or C$_{1-6}$ carboxyalkyl;
R$^{21}$ is C$_{1-4}$ sulfoalkyl or C$_{1-6}$ carboxyalkyl;
R$^{22}$ is C$_{1-4}$ alkyl, C$_{1-4}$ sulfoalkyl or C$_{1-6}$ carboxyalkyl;
E$^2$, E$^3$ and E$^4$ are independently H or C$_{1-4}$ alkyl.

The dyes of Formulae IIId, IIIe and IIIf are preferably chosen such that one or more of R$^{19}$-R$^{22}$ is C$_{1-4}$ sulfoalkyl.

Preferred specific dyes of Formula IIId are DY-631 and DY-633:

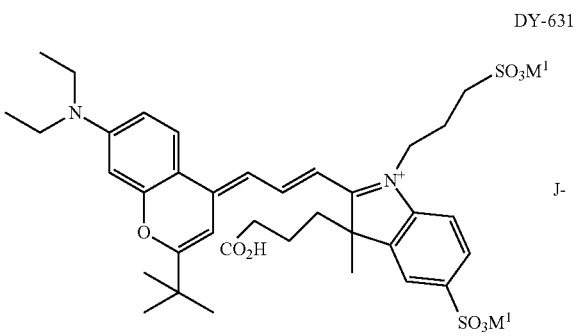

A preferred specific dye of Formula IIIe is DY-652:

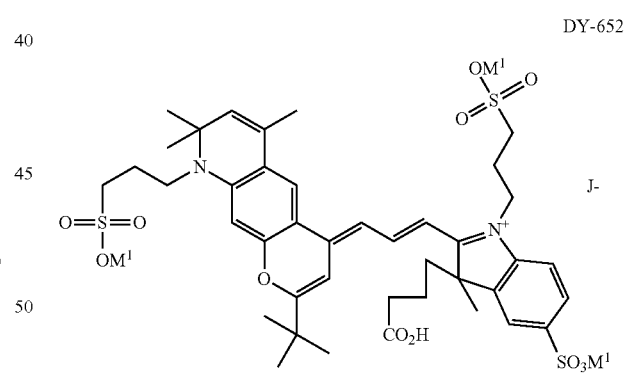

Preferred specific dyes are DY-631 and DY-652, with DY-652 being most preferred.

When a synthetic linker group (L) is present, it preferably comprises terminal functional groups which facilitate conjugation to [Bzp$^M$] and Z$^1$-[cMBP]-Z$^2$. When L comprises a peptide chain of 1 to 10 amino acid residues, the amino acid residues are preferably chosen from glycine, lysine, arginine, aspartic acid, glutamic acid or serine. When L comprises a PEG moiety, it preferably comprises units derived from oligomerisation of the monodisperse PEG-like structures of Formulae Bio1 or Bio2:

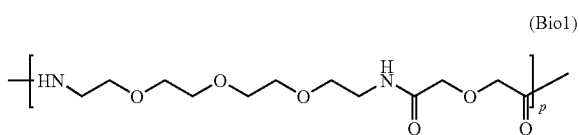

17-amino-5-oxo-6-aza-3, 9, 12, 15-tetraoxaheptadecanoic acid of Formula Bio1 wherein p is an integer from 1 to 10. Alternatively, a PEG-like structure based on a propionic acid derivative of Formula Bio2 can be used:

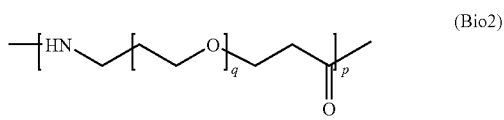

where p is as defined for Formula Bio1 and q is an integer from 3 to 15.

In Formula Bio2, p is preferably 1 or 2, and q is preferably 5 to 12.

When the linker group does not comprise PEG or a peptide chain, preferred L groups have a backbone chain of linked atoms which make up the $-(A)_m-$ moiety of 2 to 10 atoms, most preferably 2 to 5 atoms, with 2 or 3 atoms being especially preferred. A minimum linker group backbone chain of 2 atoms confers the advantage that the imaging moiety is well-separated so that any undesirable interaction is minimised.

In Formula I, n is preferably 0 or 1, most preferably 0, i.e. no linker group is present.

Preferred imaging agents of the present invention are of Formula IV:

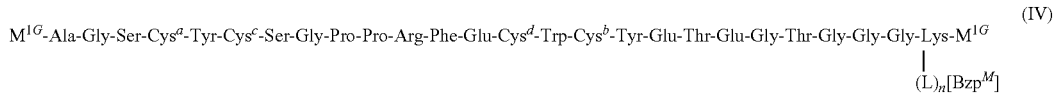

wherein the $(L)_n[Bzp^M]$ group is attached to the epsilon amino group of the Lys residue. Preferred imaging agents of Formula IV have $M^{IG}$ (N-terminal Ala) equal to acetyl and $M^{IG}$ (C-terminal Lys) equal to primary amide. In Formula IV, n is preferably zero and $Bzp^M$ is preferably of Formula IIIa or IIIb, more preferably of Formula IIIc, IIId or IIIe, most preferably the specific dyes DY-631, DY-633 or DY-652. In Formula IV, the most preferred specific dye is DY-652.

Peptides of formula $Z^1$-[cMBP]-$Z^2$ of the present invention may be obtained by a method of preparation which comprises:
(i) solid phase peptide synthesis of a linear peptide which has the same peptide sequence as the desired cMBP peptide and in which the $Cys^a$ and $Cys^b$ are unprotected, and the $Cys^c$ and $Cys^d$ residues have thiol-protecting groups;
(ii) treatment of the peptide from step (i) with aqueous base in solution to give a monocyclic peptide with a first disulfide bond linking $Cys^a$ and $Cys^b$;
(iii) removal of the $Cys^c$ and $Cys^d$ thiol-protecting groups and cyclisation to give a second disulfide bond linking $Cys^c$ and $Cys^d$, which is the desired bicyclic peptide product $Z^1$-[cMBP]-$Z^2$.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Amine protecting groups are well known to those skilled in the art and are suitably chosen from: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl). Suitable thiol protecting groups are Trt (Trityl), Acm (acetamidomethyl), t-Bu (tert-butyl), tert-Butylthio, methoxybenzyl, methylbenzyl or Npys (3-nitro-2-pyridine sulfenyl). The use of further protecting groups are described in 'Protective Groups in Organic Synthesis', Theorodora W. Greene and Peter G. M. Wuts, (John Wiley & Sons, 1991). Preferred amine protecting groups are Boc and Fmoc, most preferably Boc. Preferred amine protecting groups are Trt and Acm.

Examples 1 and 2 provide further specific details. Further details of solid phase peptide synthesis are described in P. Lloyd-Williams, F. Albericio and E. Girald; *Chemical Approaches to the Synthesis of Peptides and Proteins*, CRC Press, 1997. The cMBP peptides are best stored under inert atmosphere and kept in a freezer. When used in solution, it is best to avoid pH above 7 since that risks scrambling of the disulfide bridges.

The imaging agents can be prepared as described in the third aspect (below).

In a second aspect, the present invention provides a pharmaceutical composition which comprises the imaging agent of the first aspect together with a biocompatible carrier, in a form suitable for mammalian administration.

The "biocompatible carrier" is a fluid, especially a liquid, in which the imaging agent can be suspended or dissolved, such that the composition is physiologically tolerable, ie. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). Preferably the biocompatible carrier is pyrogen-free water for injection or isotonic saline.

The imaging agents and biocompatible carrier are each supplied in suitable vials or vessels which comprise a sealed container which permits maintenance of sterile integrity, plus optionally an inert headspace gas (eg. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour.

Preferred multiple dose containers comprise a single bulk vial (e.g. of 10 to 30 cm$^3$ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose" and are therefore preferably a disposable or other syringe suitable for clinical use. The pharmaceutical compositions of the present invention preferably have a dosage suitable for a single patient and are provided in a suitable syringe or container, as described above.

The pharmaceutical composition may optionally contain additional excipients such as an antimicrobial preservative, pH-adjusting agent, filler, stabiliser or osmolality adjusting agent. By the term "antimicrobial preservative" is meant an agent which inhibits the growth of potentially harmful micro-organisms such as bacteria, yeasts or moulds. The antimicrobial preservative may also exhibit some bactericidal properties, depending on the dosage employed. The main role of the antimicrobial preservative(s) of the present invention is to inhibit the growth of any such micro-organism in the pharmaceutical composition. The antimicrobial preservative may, however, also optionally be used to inhibit the growth of potentially harmful micro-organisms in one or more components of kits used to prepare said composition prior to administration. Suitable antimicrobial preservative(s) include: the parabens, ie. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the composition is within acceptable limits (approximately pH 4.0 to 10.5) for human or mammalian administration. Suitable such pH-adjusting agents include pharmaceutically acceptable buffers, such as tricine, phosphate or TRIS [ie. tris(hydroxymethyl)aminomethane], and pharmaceutically acceptable bases such as sodium carbonate, sodium bicarbonate or mixtures thereof. When the composition is employed in kit form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

The pharmaceutical compositions of the second aspect may be prepared under aseptic manufacture (ie. clean room) conditions to give the desired sterile, non-pyrogenic product. It is preferred that the key components, especially the associated reagents plus those parts of the apparatus which come into contact with the imaging agent (eg. vials) are sterile. The components and reagents can be sterilised by methods known in the art, including: sterile filtration, terminal sterilisation using e.g. gamma-irradiation, autoclaving, dry heat or chemical treatment (e.g. with ethylene oxide). It is preferred to sterilise some components in advance, so that the minimum number of manipulations needs to be carried out. As a precaution, however, it is preferred to include at least a sterile filtration step as the final step in the preparation of the pharmaceutical composition.

The pharmaceutical composition of the second aspect may optionally be prepared from a kit, as described for the fourth aspect below.

In a third aspect, the present invention provides a method of preparation of the imaging agent of the first aspect, which comprises one of steps (i) to (iv):

(i) reaction of a peptide of formula $Z^1$-[cMBP]-$Z^2$ wherein $Z^1$ is H and $Z^2$ is a $M^{IG}$ with a compound of formula $J^1$-$(L)_n$-$[Bzp^M]$, to give the imaging agent of Formula I wherein $Bzp^M$ is conjugated at the $Z^1$ position;

(ii) reaction of a peptide of formula $Z^1$-[cMBP]-$Z^2$ wherein $Z^1$=$Z^2$=$M^{IG}$ and cMBP comprises an Asp or Glu residue within 4 amino acid residues of either the C- or N-cMBP peptide terminus, and all other Asp/Glu residues of the cMBP peptides are protected, with a compound of formula $J^2$-$(L)_n$-$[Bzp^M]$, to give the imaging agent of Formula I wherein $Bzp^M$ is conjugated at said Asp or Glu residue of the cMBP peptide;

(iii) reaction of a peptide of formula $Z^1$-[cMBP]-$Z^3$ wherein $Z^1$ is $M^{IG}$ and $Z^3$ is a $Z^2$ group or an activated ester and all other Asp/Glu residues of the cMBP peptides are protected, with a compound of formula $J^2$-$(L)_n$-$[Bzp^M]$, to give the imaging agent of Formula I wherein $Bzp^M$ is conjugated at the $Z^2$ position;

(iv) reaction of a peptide of formula $Z^1$-[cMBP]-$Z^2$ wherein $Z^1$=$Z^2$=$M^{IG}$ and cMBP comprises a Lys within 4 amino acid residues of either the C- or N-cMBP peptide terminus, with a compound of formula $J^1$-$(L)_n$-$[Bzp^M]$, to give the imaging agent of Formula I wherein $Bzp^M$ is conjugated at a Lys residue of the cMBP peptide;

wherein:

$Z^1$, cMBP, $Z^2$, $M^{IG}$, L, n and $Bzp^M$ are as defined in the first aspect;

$Z^3$ is a $Z^2$ group or an activated ester;

$J^1$ is a carboxylic acid, activated ester, isothiocyanate or thiocyanate group;

$J^2$ is an amine group.

By the term "activated ester" or "active ester" is meant an ester derivative of the carboxylic acid which is designed to be a better leaving group, and hence permit more facile reaction with nucleophile, such as amines. Examples of suitable active esters are: N-hydroxysuccinimide (NHS), pentafluorophenol, pentafluorothiophenol, para-nitrophenol and hydroxybenzotriazole. Preferred active esters are N-hydroxysuccinimide or pentafluorophenol esters.

$J^2$ is preferably a primary or secondary amine group, most preferably a primary amine group.

The compound $Z^1$-[cMBP]-$Z^2$ preferably has both $Z^1$ and $Z^2$ equal to $M^{IG}$. Preferred cMBP peptides and $Z^1$/$Z^2$ groups are as described in the first aspect. In particular, it is preferred that the cMBP peptide comprises an Asp, Glu or Lys residue to facilitate conjugation as described for the preferred cMBP peptides of the first aspect. It is especially preferred that the cMBP peptide comprises a Lys residue, as described in step (iv).

The preparation of the $Z^1$-[cMBP]-$Z^2$ is described in the first embodiment (above). The $Z^1$-[cMBP]-$Z^3$ peptide where $Z^3$ is an active ester can be prepared from $Z^1$-[cMBP]-$Z^2$, where $Z^2$ is OH or a biocompatible cation ($B^c$), by conventional methods.

For conjugation with the cMBP, the $Bzp^M$ suitably comprises a reactive or functional group (G) group which reacts with a complementary group of the cMBP peptide forming a covalent linkage between the dye and the cMBP peptide. G may be a reactive group ($Q^a$) that may react with a complementary functional group of the peptide, or alternatively may include a functional group that may react with a reactive group of the cMBP peptide. Examples of reactive and functional groups include: active esters; isothiocyanate; maleimide; haloacetamide; acid halide; hydrazide; vinylsulfone; dichlorotriazine; phosphoramidite; hydroxyl; amino; sulfydryl; carbonyl; carboxylic acid and thiophosphate. Preferably G is a reactive group ($Q^a$). $Q^a$ is preferably an active ester.

Benzopyrylium dyes ($Bzp^M$) functionalised suitable for conjugation to cMBP are commercially available from Dyomics (Dyomics GmbH, Winzerlaer Str. 2A, D-07745 Jena, Germany; www.dyomics.com), where the reactive group ($Q^a$) is NHS ester, maleimide, amino or carboxylic acid. Precursors suitable for the synthesis of benzopyrylium dyes can also be prepared as described in U.S. Pat. No. 5,405,976. Methods of conjugating optical reporter dyes, to amino acids and peptides are described by Licha [Topics Curr. Chem., 222, 1-29 (2002); Adv. Drug Deliv. Rev., 57, 1087-1108 (2005)], as well as Flanagan et al [Bioconj. Chem., 8, 751-756 (1997)]; Lin et al, [ibid, 13, 605-610 (2002)] and Zaheer [Mol. Imaging, 1(4), 354-364 (2002)]. Methods of conjugating the linker group (L) to the cMBP peptide use analogous chemistry to that of the dyes alone (see above), and are known in the art.

In a fourth aspect, the present invention provides a kit for the preparation of the pharmaceutical composition of the second aspect, which comprises the imaging agent of the first aspect in sterile, solid form such that, upon reconstitution with a sterile supply of the biocompatible carrier of the second aspect, dissolution occurs to give the desired pharmaceutical composition.

In that instance, the imaging agent, plus other optional excipients as described above, may be provided as a lyophilised powder in a suitable vial or container. The agent is then designed to be reconstituted with the desired biocompatible carrier to the pharmaceutical composition in a sterile, apyrogenic form which is ready for mammalian administration. A preferred sterile, solid form of the imaging agent is a lyophilised solid. The sterile, solid form is preferably supplied in a pharmaceutical grade container, as described for the pharmaceutical composition (above). When the kit is lyophilised, the formulation may optionally comprise a cryoprotectant chosen from a saccharide, preferably mannitol, maltose or tricine.

In a fifth aspect, the present invention provides a method of in vivo optical imaging of the mammalian body which comprises use of either the imaging agent of the first aspect or the pharmaceutical composition of the second aspect to obtain images of sites of cMet over-expression or localisation in vivo.

The term "optical imaging" has the same meaning as for the first aspect (above). The mammalian body of the fifth aspect is preferably the human body. Preferred embodiments of the imaging agent are as described for the first aspect (above).

In the method of the fifth aspect, the imaging agent or pharmaceutical composition has preferably been previously administered to said mammalian body. By "previously administered" is meant that the step involving the clinician, wherein the imaging agent is given to the patient eg. as an intravenous injection, has already been carried out prior to imaging. This embodiment includes the use of the imaging agent of the first embodiment for the manufacture of a diagnostic agent for optical imaging in vivo of disease states of the mammalian body where cMet is implicated.

A preferred optical imaging method of the fifth aspect is Fluorescence Reflectance Imaging (FRI). In FRI, the imaging agent of the present invention is administered to a subject to be diagnosed, and subsequently a tissue surface of the subject is illuminated with an excitation light—usually continuous wave (CW) excitation. The light excites the dye ($Bzp^M$). Fluorescence from the imaging agent, which is generated by the excitation light, is detected using a fluorescence detector. The returning light is preferably filtered to separate out the fluorescence component (solely or partially). An image is formed from the fluorescent light. Usually minimal processing is performed (no processor to compute optical parameters such as lifetime, quantum yield etc.) and the image maps the fluorescence intensity. The imaging agent is designed to concentrate in the disease area, producing higher fluorescence intensity. Thus the disease area produces positive contrast in a fluorescence intensity image. The image is preferably obtained using a CCD camera or chip, such that real-time imaging is possible.

The wavelength for excitation varies depending on the type of dye used. The apparatus for generating the excitation light may be a conventional excitation light source such as: a laser (e.g., ion laser, dye laser or semiconductor laser); halogen light source or xenon light source. Various optical filters may optionally be used to obtain the optimal excitation wavelength.

A preferred FRI method comprises the steps as follows:
(i) a tissue surface of interest within the mammalian body is illuminated with an excitation light;
(ii) fluorescence from the imaging agent, which is generated by excitation of the dye ($Bzp^M$), is detected using a fluorescence detector;
(iii) the light detected by the fluorescence detector is optionally filtered to separate out the fluorescence component;
(iv) an image of said tissue surface of interest is formed from the fluorescent light of steps (ii) or (iii).

In step (i), the excitation light is preferably continuous wave (CW) in nature. In step (iii), the light detected is preferably filtered. An especially preferred FRI method is fluorescence endoscopy.

An alternative imaging method of the fifth aspect uses FDPM (frequency-domain photon migration). This has advantages over continuous-wave (CW) methods where greater depth of detection of the imaging agent within tissue is important [Sevick-Muraca. et al, Curr. Opin. Chem. Biol., 6, 642-650 (2002)]. For such frequency/time domain imaging, it is advantageous if the $Bzp^M$ has fluorescent properties which can be modulated depending on the tissue depth of the lesion to be imaged, and the type of instrumentation employed.

The FDPM method is as follows:
(a) exposing light-scattering biological tissue of said mammalian body having a heterogeneous composition to light from a light source with a pre-determined time varying intensity to excite the imaging agent, the tissue multiply-scattering the excitation light;
(b) detecting a multiply-scattered light emission from the tissue in response to said exposing;
(c) quantifying a fluorescence characteristic throughout the tissue from the emission by establishing a number of values with a processor, the values each corresponding to a level of the fluorescence characteristic at a different position within the tissue, the level of the fluorescence characteristic varying with heterogeneous composition of the tissue; and
(d) generating an image of the tissue by mapping the heterogeneous composition of the tissue in accordance with the values of step (c).

The fluorescence characteristic of step (c) preferably corresponds to uptake of the imaging agent and preferably further comprises mapping a number of quantities corresponding to adsorption and scattering coefficients of the tissue before administration of the imaging agent. The fluorescence characteristic of step (c) preferably corresponds to at least one of fluorescence lifetime, fluorescence quantum efficiency, fluorescence yield and imaging agent uptake. The fluorescence characteristic is preferably independent of the intensity of the emission and independent of imaging agent concentration.

The quantifying of step (c) preferably comprises: (i) establishing an estimate of the values, (ii) determining a calculated emission as a function of the estimate, (iii) comparing the calculated emission to the emission of said detecting to determine an error, (iv) providing a modified estimate of the fluorescence characteristic as a function of the error. The quantifying preferably comprises determining the values from a mathematical relationship modelling multiple light-scattering behaviour of the tissue. The method of the first option preferably further comprises monitoring a metabolic property of the tissue in vivo by detecting variation of said fluorescence characteristic.

The optical imaging of the fifth aspect is preferably used to help facilitate the management of colorectal cancer (CRC). By the term "management of CRC" is meant use in the: detection, staging, diagnosis, monitoring of disease progression or the monitoring of treatment. Further details of suitable optical imaging methods have been reviewed by Sevick-Muraca et al [Curr. Opin. Chem. Biol., 6, 642-650 (2002)].

In a sixth aspect, the present invention provides a method of detection, staging, diagnosis, monitoring of disease progression or in the monitoring of treatment of colorectal cancer (CRC) of the mammalian body which comprises the in vivo optical imaging method of the fifth aspect.

The invention is illustrated by the non-limiting Examples detailed below. Example 1 provides the synthesis of a biological targeting peptide (Peptide 1), which binds to cMet. Example 2 provides methods of conjugating $Bzp^M$ dyes of the invention to peptides, in particular Peptide 1. Example 3 provides data demonstrating that the peptide conjugates of Peptide 1 of the invention retain affinity for cMet, i.e. that the conjugated dye does not interfere with the biological binding and selectivity. Appropriate low binding to human serum albumin and high stability in plasma was demonstrated. Example 4 shows that the peptide conjugates of the invention exhibit useful tumour:background ratios in an animal model of colorectal cancer. Example 5 describes the use of predictive software for the dyes of the invention, and demonstrates that the dyes of the invention lack potentially dangerous metabolites in vivo. Example 6 describes the toxicity testing of Compound 6, showing that the anticipated clinical dose was well tolerated and without any drug substance related adverse effects.

TABLE 1

Structures of Benzopyrylium dyes of the Examples.

| Formula | DY-630 IIId | DY-631 IIId | DY-633 IIId | DY-650 IIIe | DY-651 IIIe | DY-652 IIIe |
|---|---|---|---|---|---|---|
| $R^{17}$ | Et | Et | Et | — | — | — |
| $R^{18}$ | Et | Et | $R^d$ | — | — | — |
| $R^{19}$ | $Bu^t$ | $Bu^t$ | $Bu^t$ | $Bu^t$ | $Bu^t$ | $Bu^t$ |
| $R^{20}$ | $CH_3$ | $R^e$ | $CH_3$ | $CH_3$ | $R^e$ | $R^e$ |
| $R^{21}$ | $R^f$ | $R^d$ | $R^f$ | $R^f$ | $R^d$ | $R^d$ |
| $R^{22}$ | — | — | — | Et | Et | $R^d$ |
| $E^2$ | — | — | — | $CH_3$ | $CH_3$ | $CH_3$ |
| $E^3$ | — | — | — | $CH_3$ | $CH_3$ | $CH_3$ |
| $E^4$ | — | — | — | $CH_3$ | $CH_3$ | $CH_3$ | where: $R^d$ is —$(CH_2)_3SO_3H$, $R^e$ is —$(CH_2)_3CO_2H$ and $R^f$ is —$(CH_2)_5CO_2H$.

DY-752 has the same rings and substituent pattern as DY-652, but has a pentamethine linkage (i.e. w=2 and $R^5$=H) in place of the trimethine linkage of DY-652.

Abbreviations

Conventional 3-letter and single letter amino acid abbreviations are used.

Acm: Acetamidomethyl
ACN: Acetonitrile
Boc: tert-Butyloxycarbonyl
DMF: N,N'-Dimethylformamide
DMSO: Dimethylsulfoxide
Fmoc: 9-Fluorenylmethoxycarbonyl
HCl: Hydrochloric acid
HPLC: High performance liquid chromatography
HSPyU O-(N-succinimidyl)-N,N,N',N'-tetramethyleneuronium hexafluorophosphate
Ile: Isoleucine
LC-MS: Liquid chromatography mass spectroscopy
NHS: N-hydroxy-succinimide
NMM: N-Methylmorpholine
NMP: 1-Methyl-2-pyrrolidinone
Pbf: 2,2,4,6,7-Pentamethyldihydrobenzofuran-5-sulfonyl
PBS: Phosphate-buffered saline.
TFA: Trifluoroacetic acid
Trt: Trityl
TSTU: O-(N-Succinimidyl)-N,N,N',N'-tetramethyluronium tetrafluoroborate.

EXAMPLE 1

Synthesis of Peptide 1

A 26-mer bicyclic peptide having 2 Cys-Cys bonds (Cys4-16 and 6-14) having the following sequence was used:

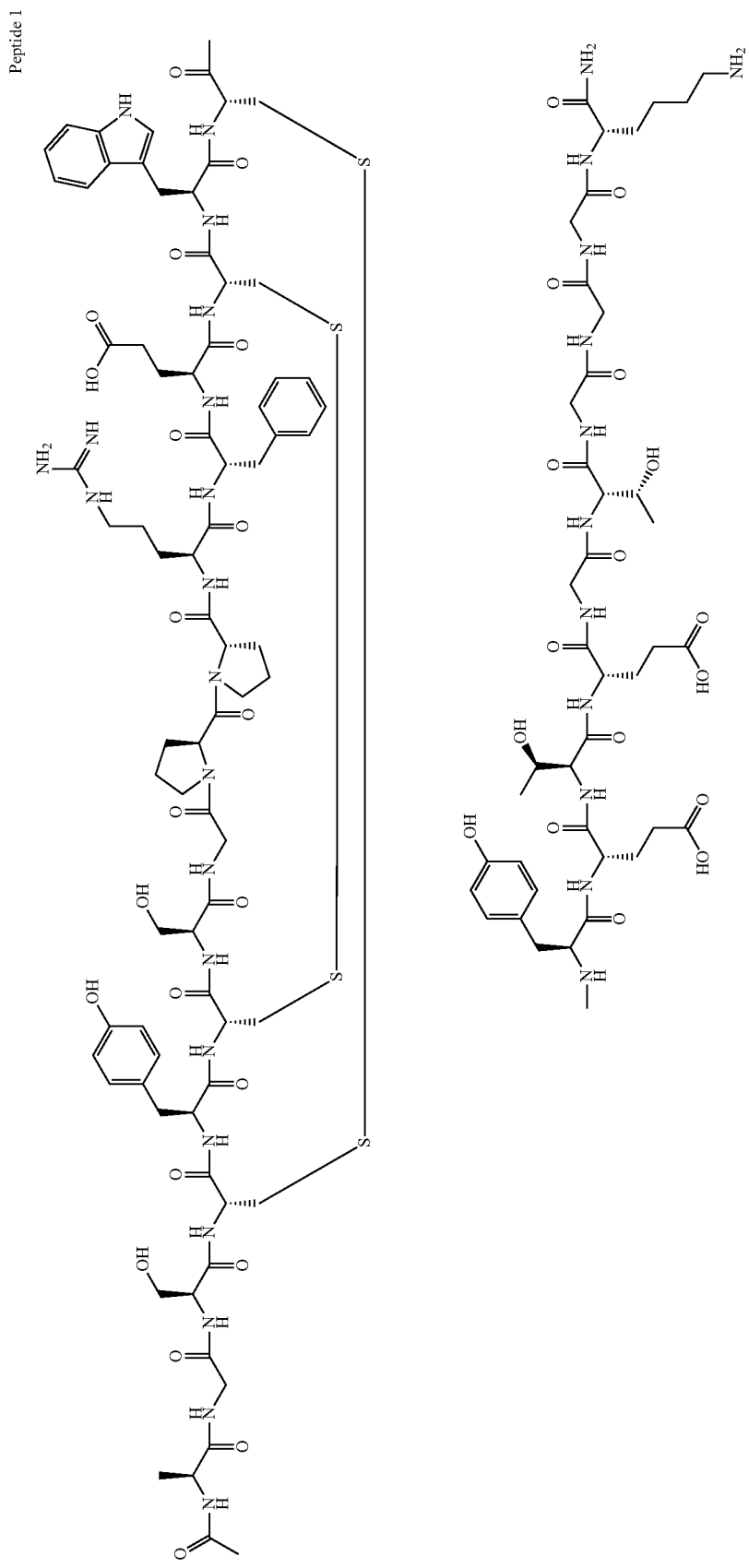

("Peptide 1")
Ac-Ala-Gly-Ser-Cys-Tyr-Cys-Ser-Gly-Pro-Pro-Arg-Phe-Glu-Cys-Trp-Cys-Tyr-Glu-Thr-Glu-Gly-Thr-Gly-Gly-Gly-Lys-NH$_2$.

Step (a): Synthesis of Protected Linear Precursor of Peptide 1.

The precursor linear peptide has the sequence:
Ac-Ala-Gly-Ser-Cys-Tyr-Cys(Acm)-Ser-Gly-Pro-Pro-Arg-Phe-Glu-Cys(Acm)-Trp-Cys-Tyr-Glu-Thr-Glu-Gly-Thr-Gly-Gly-Gly-Lys-NH$_2$.

The peptidyl resin H-Ala-Gly-Ser(tBu)-Cys(Trt)-Tyr(tBu)-Cys(Acm)-Ser(tBu)-Gly-Pro-Pro-Arg(Pbf)-Phe-Glu(OtBu)-Cys(Acm)-Trp(Boc)-Cys(Trt)-Tyr(tBu)-Glu(OtBu)-Thr($\psi^{MeMe}$pro)-Glu(OtBu)-Gly-Thr(tBu)-Gly-Gly-Gly-Lys(Boc)-Polymer was assembled on an Applied Biosystems 433A peptide synthesizer using Fmoc chemistry starting with 0.1 mmol Rink Amide Novagel resin. An excess of 1 mmol pre-activated amino acids (using HBTU) was applied in the coupling steps. Glu-Thr pseudoproline (Novabiochem 05-20-1122) was incorporated in the sequence. The resin was transferred to a nitrogen bubbler apparatus and treated with a solution of acetic anhydride (1 mmol) and NMM (1 mmol) dissolved in DCM (5 mL) for 60 min. The anhydride solution was removed by filtration and the resin washed with DCM and dried under a stream of nitrogen.

The simultaneous removal of the side-chain protecting groups and cleavage of the peptide from the resin was carried out in TFA (10 mL) containing 2.5% TIS, 2.5% 4-thiocresol and 2.5% water for 2 hours and 30 min. The resin was removed by filtration, TFA removed in vacuo and diethyl ether added to the residue. The formed precipitate was washed with diethyl ether and air-dried affording 264 mg of crude peptide.

Purification by preparative HPLC (gradient: 20-30% B over 40 min where A=H$_2$O/0.1% TFA and B=ACN/0.1% TFA, flow rate: 10 mL/min, column: Phenomenex Luna 5µ C18 (2) 250×21.20 mm, detection: UV 214 nm, product retention time: 30 min) of the crude peptide afforded 100 mg of pure Peptide 1 linear precursor. The pure product was analysed by analytical HPLC (gradient: 10-40% B over 10 min where A=H$_2$O/0.1% TFA and B=ACN/0.1% TFA, flow rate: 0.3 mL/min, column: Phenomenex Luna 3µ C18 (2) 50×2 mm, detection: UV 214 nm, product retention time: 6.54 min). Further product characterisation was carried out using electrospray mass spectrometry (MH$_2^{2+}$ calculated: 1464.6, MH$_2^{2+}$ found: 1465.1).

Step (b): Formation of Cys4-16 Disulfide Bridge.

Cys4-16; Ac-Ala-Gly-Ser-Cys-Tyr-Cys(Acm)-Ser-Gly-Pro-Pro-Arg-Phe-Glu-Cys(Acm)-Trp-Cys-Tyr-Glu-Thr-Glu-Gly-Thr-Gly-Gly-Gly-Lys-NH$_2$.

The linear precursor from step (a) (100 mg) was dissolved in 5% DMSO/water (200 mL) and the solution adjusted to pH 6 using ammonia. The reaction mixture was stirred for 5 days. The solution was then adjusted to pH 2 using TFA and most of the solvent removed by evaporation in vacuo. The residue (40 mL) was injected in portions onto a preparative HPLC column for product purification.

Purification by preparative HPLC (gradient: 0% B for 10 min, then 0-40% B over 40 min where A=H$_2$O/0.1% TFA and B=ACN/0.1% TFA, flow rate: 10 mL/min, column: Phenomenex Luna 5µ C18 (2) 250×21.20 mm, detection: UV 214 nm, product retention time: 44 min) of the residue afforded 72 mg of pure Peptide 1 monocyclic precursor. The pure product (as a mixture of isomers P1 to P3) was analysed by analytical HPLC (gradient: 10-40% B over 10 min where A=H$_2$O/0.1% TFA and B=ACN/0.1% TFA, flow rate: 0.3 mL/min, column: Phenomenex Luna 3µ C18 (2) 50×2 mm, detection: UV 214 nm, product retention time: 5.37 min (P1); 5.61 min (P2); 6.05 min (P3)). Further product characterisation was carried out using electrospray mass spectrometry (MH$_2^{2+}$ calculated: 1463.6, MH$_2^{2+}$ found: 1464.1 (P1); 1464.4 (P2); 1464.3 (P3).

Step (c): Formation of Cys6-14 Disulfide Bridge (Peptide 1).

The monocyclic precursor from step (b) (72 mg) was dissolved in 75% AcOH/water (72 mL) under a blanket of nitrogen. 1 M HCl (7.2 mL) and 0.05 M I$_2$ in AcOH (4.8 mL) were added in that order and the mixture stirred for 45 min. 1 M ascorbic acid (1 mL) was added giving a colourless mixture. Most of the solvents were evaporated in vacuo and the residue (18 mL) diluted with water/0.1% TFA (4 mL) and the product purified using preparative HPLC.

Purification by preparative HPLC (gradient: 0% B for 10 min, then 20-30% B over 40 min where A=H$_2$O/0.1% TFA and B=ACN/0.1% TFA, flow rate: 10 mL/min, column: Phenomenex Luna 5µ C18 (2) 250×21.20 mm, detection: UV 214 nm, product retention time: 43-53 min) of the residue afforded 52 mg of pure Peptide 1. The pure product was analysed by analytical HPLC (gradient: 10-40% B over 10 min where A=H$_2$O/0.1% TFA and B=ACN/0.1% TFA, flow rate: 0.3 mL/min, column: Phenomenex Luna 3µ C18 (2) 50×2 mm, detection: UV 214 nm, product retention time: 6.54 min). Further product characterisation was carried out using electrospray mass spectrometry (MH$_2^{2+}$ calculated: 1391.5, MH$_2^{2+}$ found: 1392.5).

EXAMPLE 2

Synthesis of Peptide Conjugates of Benzopyrylium Dyes

General Conjugation Method.

To a solution of Peptide 1 (from Example 1; 4 mg, 1.4 µmol) in DMF (0.5 mL) was added a solution of Bzp$^M$ NHS ester (1 mg, 1 µmol) and sym.-collidine (8 µL, 60 µmol) in DMF (0.5 mL). The reaction mixture was heated (microwave assisted) at 60° C. for 1 hr, then at RT overnight. The reaction mixture was then diluted with 20% ACN/water/0.1% TFA (7 mL) and the product purified using preparative HPLC.

Purification and Characterisation.

Purification by preparative HPLC (gradient: 20-40% B over 40 min where A=H$_2$O/0.1% TFA and B=ACN/0.1% TFA, flow rate: 10 mL/min, column: Phenomenex Luna 5µ C18 (2) 250×21.2 mm, detection: UV 214 nm) of the crude peptide afforded pure [Peptide 1]-Bzp$^M$ conjugate. The pure product was analysed by analytical HPLC (gradient: 10-40% B over 5 min where A=H$_2$O/0.1% TFA and B=ACN/0.1% TFA, flow rate: 0.6 mL/min, column: Phenomenex Luna 3µ C18 (2) 20×2 mm, detection: UV 214 nm). Further product characterisation was carried out using electrospray mass spectrometry. The compounds prepared are given in Table 3:

TABLE 3

Peptide-dye conjugates of Peptide 1.

| Compound | Bzp$^M$ | Synthesis yield | MS found (MS theoretical) |
|---|---|---|---|
| 1 | DY-630 | 2.1 mg (44%) | 1700.7 (MH$^{2+}$ 1699.7) |
| 2 | DY-631 | 2.5 mg (60%) | 1740.2 (MH$^{2+}$ 1739.7) |
| 3 | DY-633 | 2.5 mg (60%) | 1747.4 (MH$^{2+}$ 1746.7) |
| 4 | DY-650 | 3.1 mg (69%) | 1726.1 (MH$^{2+}$ 1725.7) |
| 5 | DY-651 | 3.0 mg (77%) | 1766.4 (MH$^{2+}$ 1765.7) |
| 6 | DY-652 | 3.3 mg (91%) | 1813.5 (MH$^{2+}$ 1812.7) |
| 7 | DY-752 | 1.8 mg (45%) | 1825.9 (MH$^{2+}$ 1825.7) |

EXAMPLE 3

In Vitro Fluorescence Polarisation Assay

Fluorescence polarisation assay was used to examine the affinity binding of the imaging agent towards the cMet target as well as the binding properties related to plasma proteins. The principle of the fluorescence polarisation method can briefly be described as follows:

Monochromatic light passes through a horizontal polarizing filter and excites fluorescent molecules in the sample. Only those molecules that oriented properly in the vertically polarized plane adsorb light, become excited, and subsequently emit light. The emitted light is measured in both horizontal and vertical planes. The anisotropy value (A), is the ratio between the light intensities following the equation $$A = \frac{\text{Intensity with horizontal polarizer} - \text{Intensity with vertical polarizer}}{\text{Intensity with horizontal polarizer} + 2*\text{Intensity with vertical polarizer}}$$

The fluorescence anisotropy measurements were performed in 384-well microplates in a volume of 10 µL in binding buffer (PBS, 0.01% Tween-20, pH 7.5) using a Tecan Safire fluorescence polarisation plate reader (Tecan, US) at Ex 635/Em 678 nm. The to concentration of dye-labelled peptide was held constant (5 nM) and the concentration of the human c-Met/Fe chimera (R&D Systems) was varied from 0-250 nM. Binding mixtures were equilibrated in the microplate for 10 min at 30° C. The observed change in anisotropy was fit to the equation $$r_{obs} = r_{free} + (r_{bound} - r_{free})\frac{(K_D + cMet + P) - \sqrt{(K_D + cMet + P)2 - 4 \cdot cMet \cdot P}}{2 \cdot P}$$

where robs is the observed anisotropy, rfree is the anisotropy of the free peptide, rbound is the anisotropy of the bound peptide, $K_d$ is the dissociation constant, cMet is the total c-Met concentration, and P is the total dye-labelled peptide concentration. The equation assumes that the synthetic peptide and the receptor form a reversible complex in solution with 1:1 stoichiometry. Data fitting was done via nonlinear regression using SigmaPlot software to obtain the $K_d$ value (one-site binding).

Compounds 1 to 6 were tested for binding towards human c-Met (Fc chimera). The results showed a $K_d$ of nM for the binding of all compounds tested to human c-Met (see Table 4).

The change of the polarization value was used to assess the binding of the Compound to human serum albumin as a low change of polarisation value is associated to low binding being appropriate for in-vivo use. The plasma protein binding (PPB) was confirmed with Biacore measurements. The stability of the imaging agent in plasma was confirmed by measuring the amount of the Compound left after incubation in mouse plasma for 2 hours at 37° C.

TABLE 4 in vitro properties of Compounds 1-6.

| Compound | Affinity (Kd, nM) | PPB (% change in polarisation value) | Binding human serum albumin (Biacore) | Mouse plasma stability (2 h, 37° C.) |
|---|---|---|---|---|
| 1 | 2.2 | 36 | Very high | >95% |
| 2 | 0.5 | 33 | Very low | >95% |
| 3 | 0.5 | 27 | Low | >95% |
| 4 | 3.2 | 55 | Very high | >95% |
| 5 | 2.2 | 49 | Medium | >95% |
| 6 | 0.9 | 46 | Very low | >95% |

EXAMPLE 4

In Vivo Testing of Compounds 2 to 6

(a) Animal Model.

Female BALB c/A nude (Born) mice were used in the study. The use of the animals was approved by the local ethics committee. BALB c/A nude is an inbred immunocompromised mouse strain with a high take rate for human tumours as compared to other nude mice strains. The mice were 8 weeks old upon arrival and with a body weight of approx. 20 grams at the start of the study. The animals were housed in individually ventilated cages (IVC, Scanbur BK) with HEPA filtered air. The animals had ad libitum access to "Rat and Mouse nr. 3 Breeding" diet (Scanbur BK) and tap water acidified by addition of HCl to a molar concentration of 1 mM (pH 3.0).

The colon cancer cell HT-29 is derived from human colon carcinomas and is reported to express c-Met according to Zeng et al [Clip. Exp. Metastasis, 21, 409-417. (2004)]. The cell line was proven to be tumorigenic when inoculated subcutaneously into nude mice [Flatmark et al, Eur. J. Cancer 40, 1593-1598 (2004)].

HT-29 cells were grown in McCoy's 5a medium (Sigma #M8403) supplemented with 10% fetal bovine serum and penicillin/streptomycin. Stocks were made at passage number four (P4) and frozen down for storage in liquid nitrogen at $10^7$ cells/vial in the respective culture media containing 5% DMSO. On the day of the transplantation, the cells were thawed quickly in 37° C. water bath (approx. 2 min), washed and resuspended in PBS/2% serum (centrifugation at 1200 rpm for 10 min). Thorough mixing of cells in the vials was ensured every time the cells were aspirated into the dosing syringe. A volume of 0.1 ml of cell suspension was injected s.c. at the shoulder and at the back using a fine bore needle (25 G). The animals were then returned to their cages and the tumours were allowed to grow for 13-17 days. The animals were allowed an acclimatisation period of at least 5 days before the inoculation procedure.

(b) Procedure.

All test substances were reconstituted with PBS from freeze-dried powder. A small stack of white printer paper was imaged to obtain a flat field image which was used to correct for illumination inhomogeneities. For immobilisation during the optical imaging procedure, the animals were anaesthetized in a coaxial open mask to light surgical level anaesthesia with Isoflurane (typically 1.3-2%), using oxygen as the carrier gas. A small piece of skin (3-5 mm) was removed over parts of the tumour and adjacent muscle using a surgical forceps and fine scissors while the animal was anaesthetized. This was done to measure the signal from tumour and muscle without interference from the overlying skin tissue. The wound was covered by applying a liquid, non-fluorescent bandage spray (3M, MN, USA).

The respiration and body temperature of the animal was monitored with a BioVet system (m2m Imaging Corp, NJ, USA) using a pneumatic sensor underneath the animal and a rectal temperature probe. The BioVet system also supplied external heating using a heating mat set to 40° C. to sustain normal body temperature for the duration of the imaging procedure (2 hours). A Venflon catheter was placed in the tail vein for contrast agent administration. Each animal was given one contrast agent injection. The injected volume was 0.1 ml of test compound followed immediately by a 0.2 ml saline flush. Fluorescence images were acquired just prior to injection and then every 30 seconds for 2 hours.

(c) Imaging.

Imaging was performed through a clinical laparoscope adapted to use a light source to excite the reporter and a filtering system to extract the fluorescence component. A 635 nm laser was used for excitation of the reporter molecule. A Hamamatsu ORCA ERG CCD camera was used as the detector. The camera was operated in 2×2 binning mode with 0 gain. Standard exposure time for colon imaging was 4 s. The intensity distribution in the image was corrected for illumination inhomogeneities through system calibration data. A target to background ratio was computed from regions of interest placed over the exposed tumour and normal muscle background.

(d) Results.

The test Compounds had the following average tumour:muscle ratios (Table 5):

TABLE 5 tumour:muscle ratios of Compounds 2 to 6.

| Compound | Average tumour:muscle ratio (2 hours p.i.) |
|---|---|
| 2 | 2.40 |
| 3 | 1.67 |
| 4 | 1.52 |
| 5 | 1.22 |
| 6 | 1.57 |

EXAMPLE 5

Metabolism and Toxicity Prediction

The software tools Derek and Meteor were obtained from Lhasa Ltd (22-23 Blenheim Terrace, Leeds LS2 9HD, UK). Derek is used for predicting toxicity of new chemical entities based on known structure-dependent toxicity. Similarly, Meteor predicts likely metabolites of novel chemicals. Both tools are based on published and unpublished (but verified) data for chemical compounds. The chemical structure of dye DY-652 was input. No potentially dangerous metabolites in vivo were predicted.

EXAMPLE 6

Toxicity Testing of Compound 6

A limited acute dose toxicity study was conducted to investigate the tolerance of Compound 6 at 100 times the preclinical imaging dose (50 nmol/kg body weight). The compound was injected intravenously in male rats, and the animals were sacrificed at 1, 14, 21 and 28 days post injection (p.i.). At necropsy, the major organs were inspected for gross pathology, and the kidneys were taken into neutral buffered formalin for subsequent histomorphological evaluation. A weak blue colouration of the skin and a moderate blue colouration of the urine were observed immediately after injection, which disappeared within 1 day p.i. At necropsy, the kidneys were diffusely green on day 1 p.i. Light microscopy showed no Compound 6-related findings in the kidneys. The other minor changes seen were incidental and common in young adult laboratory rats. Strong fluorescence staining of blood vessels in the kidney was observed on day 1 p.i. The staining was reduced by day 14 p.i. and was not discernible from control on day 21 p.i.

No evidence of degeneration, necrosis or inflammation was noted in any of the treated animals, suggesting that the nephrotoxicity of the compound is low. It was concluded to that a single intravenous administration of Compound 6 to male rats at 100 times the anticipated clinical dose was well tolerated and without any drug substance related adverse effects.

The invention claimed is:

1. An imaging agent which comprises a conjugate of Formula I:

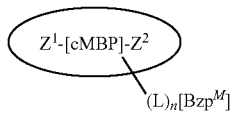

(I)

where:

$Z^1$ is attached to the N-terminus of cMBP, and is H or $M^{IG}$;

$Z^2$ is attached to the C-terminus of cMBP and is OH, $OB^c$, or $M^{IG}$, where $B^C$ is a biocompatible cation;

cMBP is a cMet binding cyclic peptide of 17 to 30 amino acids which comprises the amino acid sequence (SEQ-1):

$Cys^a$-$X^1$-$Cys^c$-$X^2$-Gly-Pro-Pro-$X^3$-Phe-Glu-$Cys^d$-Trp-$Cys^b$-Tyr-$X^4$-$X^5$-$X^6$;

wherein $X^1$ is Asn, His or Tyr;

$X^2$ is Gly, Ser, Thr or Asn;

$X^3$ is Thr or Arg;

$X^4$ is Ala, Asp, Glu, Gly or Ser;

$X^5$ is Ser or Thr;

$X^6$ is Asp or Glu;

and $Cys^{a-d}$ are each cysteine residues such that residues a and b as well as c and d are cyclised to form two separate disulfide bonds;

$M^{IG}$ is a metabolism inhibiting group which is a biocompatible group which inhibits or suppresses in vivo metabolism of the peptide; wherein when $M^{IG}$ is at the amino terminus, it is selected from N-acylated groups —NH(C=O)$R^G$ where the acyl group —(C=O)$R^G$ has $R^G$ chosen from: $C_{1-6}$ alkyl, $C_{3-10}$ aryl groups or comprises a polyethyleneglycol (PEG) building block; wherein when $M^{IG}$ is at the carboxy terminus, it is selected from carboxamide, tert-butyl ester, benzyl ester, cyclohexyl ester, amino alcohol or a polyethyleneglycol (PEG) building block;

L is a synthetic linker group of formula -(A)$_m$- wherein each A is independently —$CR_2$—, —CR=CR—, —C≡C—, —$CR_2CO_2$—, —$CO_2CR_2$—, —NRCO—, —CONR—, —NR(C=O)NR—, —NR(C=S)NR—, —$SO_2$NR—, —$NRSO_2$—, —$CR_2OCR_2$—, —$CR_2SCR_2$—, —$CR_2NRCR_2$—, a $C_{4-8}$ cycloheteroalkylene group, a $C_{4-8}$ cycloalkylene group, a $C_{5-12}$ arylene group, or a $C_{3-12}$ heteroarylene group, an amino acid, a sugar or a monodisperse polyethyleneglycol (PEG) building block;

each R is independently chosen from H, $C_{1-4}$ alkyl, $C_{2-4}$ alkenyl, $C_{2-4}$ alkynyl, $C_{1-4}$ alkoxyalkyl or $C_{1-4}$ hydroxyalkyl;

m is an integer of value 1 to 20;

n is an integer of value 0 or 1;

$Bzp^M$ is a benzopyrylium dye of Formula II:

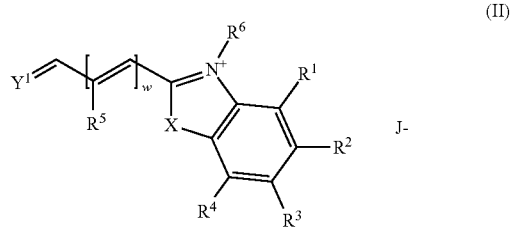

(II)

where:

Y$^1$ is a group of Formula Y$^a$ or Y$^b$

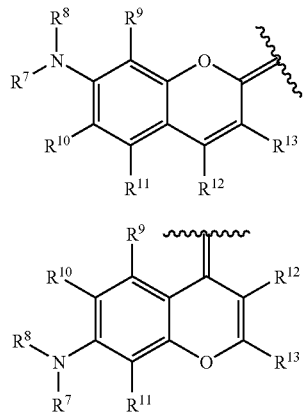

R$^1$-R$^4$ and R$^9$-R$^{13}$ are independently selected from H, —SO$_3$M$^1$, Hal, R$^a$ or C$_{3-12}$ aryl, where each M$^1$ is independently H or Bc;

R$^5$ is H, C$_{1-4}$ alkyl, C$_{3-12}$ arylsulfonyl, Cl, or R$^5$ together with one of R$^6$, R$^{14}$, R$^{15}$ or R$^{16}$ may optionally form a 5- or 6-membered unsaturated aliphatic, unsaturated heteroaliphatic or aromatic ring;

R$^6$ and R$^{16}$ are independently R$^a$ groups;

R$^7$ and R$^8$ are independently C$_{1-4}$ alkyl, C$_{1-4}$ sulfoalkyl or C$_{1-6}$ hydroxyalkyl or optionally together with one or both of R$^9$ and/or R$^{10}$ may form a 5- or 6-membered N-containing heterocyclic or heteroaryl ring;

X is —CR$^{14}$R$^{15}$—, —O—, —S—, —Se—, —NR$^{16}$— or —CH=CH—, where R$^{14}$ to R$^{16}$ are independently R$^a$ groups;

R$^a$ is C$_{1-4}$ alkyl, C$_{1-4}$ sulfoalkyl, C$_{1-6}$ carboxyalkyl or C$_{1-6}$ hydroxyalkyl;

w is 1 or 2;

J is a biocompatible anion;

with the proviso that Bzp$^M$ comprises at least one sulfonic acid substituent chosen from the R$^1$ to R$^{16}$ groups.

2. The imaging agent of claim 1, where in addition to SEQ-1, the cMBP further comprises an Asp or Glu residue within 4 amino acid residues of either the C- or N-cMBP peptide terminus, and (L)$_n$[Bzp$^M$] is functionalised with an amine group which is conjugated to the carboxyl side chain of said Asp or Glu residue to give an amide bond.

3. The imaging agent of claim 1, where in addition to SEQ-1, the cMBP comprises a Lys residue within 4 amino acid residues of either the C- or N-cMBP peptide terminus, and (L)$_n$[Bzp$^M$] is functionalised with a carboxyl group which is conjugated to the epsilon amine side chain of said Lys residue to give an amide bond.

4. The imaging agent of claim 1, wherein cMBP further comprises the amino acid sequence of either SEQ-2 or SEQ-3:

```
                                                (SEQ-2)
Ser-Cysᵃ-X¹-Cysᶜ-X²-Gly-Pro-Pro-X³-Phe-Glu-Cysᵈ-

Trp-Cysᵇ-Tyr-X⁴-X⁵-X⁶.;
```

```
                                                (SEQ-3)
Ala-Gly-Ser-Cysᵃ-X¹-Cysᶜ-X²-Gly-Pro-Pro-X³-Phe-

Glu-Cysᵈ-Trp-Cysᵇ-Tyr-X⁴-X⁵-X⁶-Gly-Thr.
```

5. The imaging agent of claim 4, wherein X$^3$ is Arg.

6. The imaging agent of claim 4, wherein in addition to SEQ-1, SEQ-2 or SEQ-3, cMBP further comprises at either the N- or C-terminus a linker peptide which is chosen from -Gly-Gly-Gly-Lys- (SEQ-4), -Gly-Ser-Gly-Lys- (SEQ-5) or -Gly-Ser-Gly-Ser-Lys- (SEQ-6).

7. The imaging agent of claim 6, where cMBP has the amino acid sequence (SEQ-7):

```
Ala-Gly-Ser-Cysᵃ-Tyr-Cysᶜ-Ser-Gly-Pro-Pro-Arg-Phe-

Glu-Cysᵈ-Trp-Cysᵇ-Tyr-Glu-Thr-Glu-Gly-Thr-Gly-Gly-

Gly-Lys.
```

8. The imaging agent of claim 1, where both Z$^1$ and Z$^2$ are independently M$^{IG}$.

9. The imaging agent of claim 8, where Z$^1$ is acetyl and Z$^2$ is a primary amide.

10. The imaging agent of claim 1, where n is 0.

11. The imaging agent of claim 1, where Bzp$^M$ is of Formula IIa:

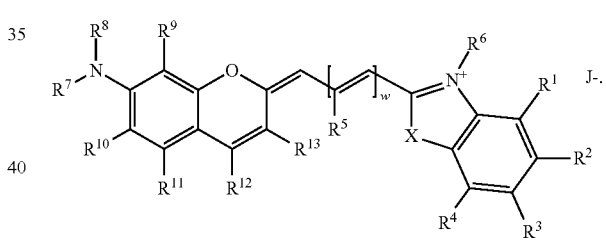

12. The imaging agent of claim 1, where Bzp$^M$ is of Formula IIb:

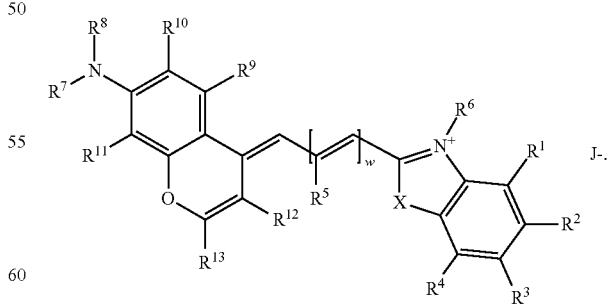

13. The imaging agent of claim 1, where the Bzp$^M$ comprises 2 to 4 sulfonic acid substituents.

14. The imaging agent of claim 1, where the Bzp$^M$ comprises at least one C$_{1-4}$ sulfoalkyl substituent.

15. The imaging agent of claim 1, where Bzp$^M$ is of Formula III:

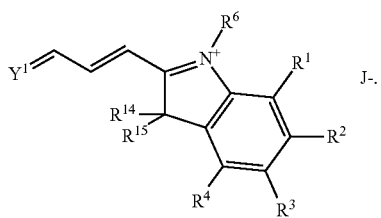

(III)

16. The imaging agent of claim 15, where Bzp$^M$ is of Formula IIIc, IIId o IIIe:

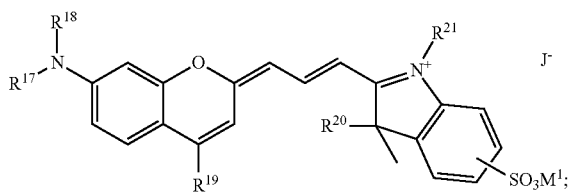

(IIIc)

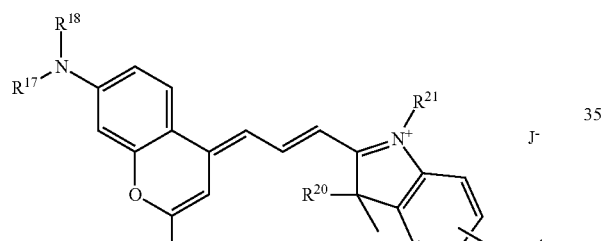

(IIId)

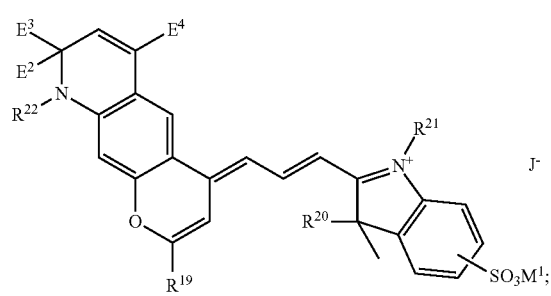

(IIIe)

where:

M$^1$ is H or B$^c$, where B$^C$ is a biocompatible cation;

R$^{17}$ and R$^{18}$ are independently chosen from C$_{1-4}$ alkyl or C$_{1-4}$ sulfoalkyl;

R$^{19}$ is H or C$_{1-4}$ alkyl;

R$^{20}$ is C$_{1-4}$ alkyl, C$_{1-4}$ sulfoalkyl or C$_{1-6}$ carboxyalkyl;

R$^{21}$ is C$_{1-4}$ sulfoalkyl or C$_{1-6}$ carboxyalkyl;

R$^{22}$ is C$_{1-4}$ alkyl, C$_{1-4}$ sulfoalkyl or C$_{1-6}$ carboxyalkyl;

E$^2$, E$^3$ and E$^4$ are independently H or C$_{1-4}$ alkyl.

17. The imaging agent of claim 1, where:
cMBP has the amino acid sequence (SEQ-7):

Ala-Gly-Ser-Cys$^a$-Tyr-Cys$^c$-Ser-Gly-Pro-Pro-Arg-Phe-Glu-Cys$^d$-Trp-Cys$^b$-Tyr-Glu-Thr-Glu-Gly-Thr-Gly-Gly-Gly-Lys;

Z$^1$ is acetyl and Z$^2$ is a primary amide and Bzp$^M$ is selected from the compounds of Formula (IIa), (IIb) and (III):

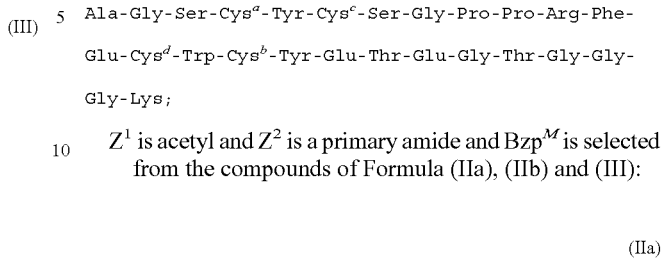

(IIa)

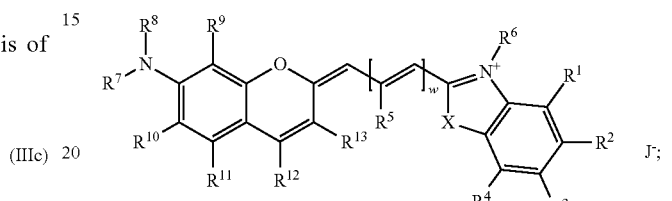

(IIb)

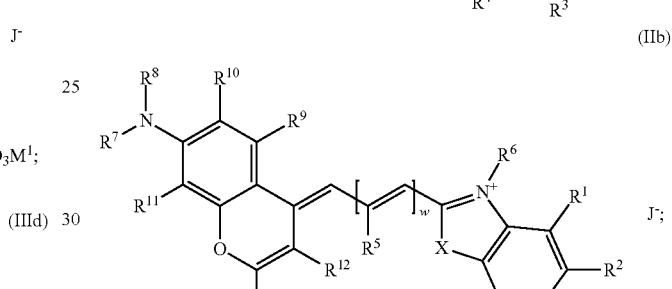

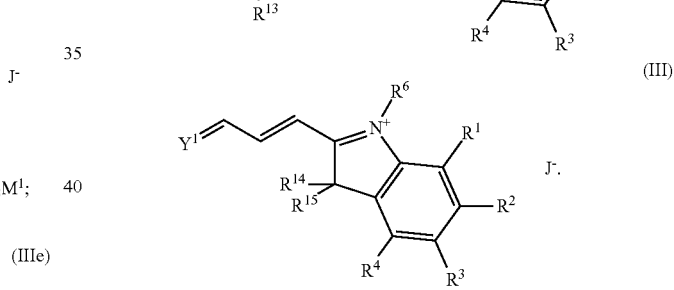

(III)

18. A pharmaceutical composition which comprises the imaging agent of claim 1, together with a biocompatible carrier, in a form for mammalian administration.

19. The pharmaceutical composition of claim 18, which has a dosage suitable for a single patient and is provided in a syringe or container.

20. A method of preparation of the imaging agent of claim 1, which comprises one of steps (i) to (ii):
(i) reaction of a peptide of formula Z$^1$-[cMBP]-Z$^2$ wherein Z$^1$ is H and Z$^2$ is a M$^{IG}$ with a compound of formula J$^1$-(L)$_n$-[Bzp$^M$], to give the imaging agent of Formula I wherein Bzp$^M$ is conjugated at the Z$^1$ position; or
(ii) reaction of a peptide of formula Z$^1$-[cMBP]-Z$^3$ wherein Z$^1$ is M$^{IG}$ and Z$^3$ is a Z$^2$ group or an activated ester and all other Asp/Glu residues of the cMBP peptides are protected, with a compound of formula J$^2$-(L)$_n$-[Bzp$^M$], to give the imaging agent of Formula I wherein Bzp$^M$ is conjugated at the Z$^2$ position;
wherein:
J$^1$ is a carboxylic acid, activated ester, isothiocyanate or thiocyanate group; and
J$^2$ is an amine group.

21. A method of preparation of the imaging agent of claim 3, which comprises:

reaction of a peptide of formula $Z^1$-[cMBP]-$Z^2$ wherein $Z^1=Z^2=M^{IG}$, with a compound of formula $J^1$-$(L)_n$[$Bzp^M$], to give the imaging agent of Formula I wherein $Bzp^M$ is conjugated at a Lys residue of the cMBP peptide;

wherein:

$J^1$ is a carboxylic acid, activated ester, isothiocyanate or thiocyanate group.

22. A kit, which comprises the imaging agent of claim 1 in sterile, solid form; and a sterile supply of a biocompatible carrier.

23. The kit of claim 22, where said sterile, solid form is a lyophilised solid.

24. A method of in vivo optical imaging of the mammalian body which comprises first administering the imaging agent of claim 1 to said mammalian body, then obtaining images of sites of cMet over-expression or localisation in vivo, which obtaining step comprises the steps of:

(i) illuminating a tissue surface of interest within the mammalian body with an excitation light;

(ii) detecting fluorescence from the imaging agent, which is generated by excitation of the $Bzp^M$, using a fluorescence detector;

(iii) optionally filtering the light detected by the fluorescence detector to separate out the fluorescence component;

(iv) forming an image of said tissue surface of interest from the fluorescent light of steps (ii) or (iii).

25. The method of claim 24 where the excitation light of step (i) is continuous wave (CW) in nature.

26. A method of in vivo optical imaging of the mammalian body which comprises first administering the imaging agent of claim 1 to said mammalian body, then obtaining images of sites of cMet over-expression or localisation in vivo, which obtaining step comprises:

(a) exposing biologic tissue of said mammalian body having a heterogeneous composition to light from a light source with a pre-determined time varying intensity to excite the imaging agent, the tissue multiply-scattering the excitation light;

(b) detecting a multiply-scattered light emission from the tissue in response to said exposing;

(c) quantifying a fluorescence characteristic throughout the tissue from the emission by establishing a number of values with a processor, the values each corresponding to a level of the fluorescence characteristic at a different position within the tissue, the level of the fluorescence characteristic varying with heterogeneous composition of the tissue; and (d) generating an image of the tissue by mapping the heterogeneous composition of the tissue in accordance with the values of step (c).

27. The method of claim 24, where the in vivo optical imaging comprises fluorescence endoscopy.

28. A method of preparation of the imaging agent of claim 2, which comprises:

reaction of a peptide of formula $Z^1$-[cMBP]-$Z^2$ wherein $Z^1=Z^2=M^{IG}$ and except said Asp or Glu residue within 4 amino acid residues of either the C- or N-cMBP peptide terminus, all other Asp/Glu residues of the cMBP peptides are protected, with a compound of formula $J^2$-$(L)_n$[$Bzp^M$], to give the imaging agent of Formula I wherein $Bzp^M$ is conjugated at said Asp or Glu residue of the cMBP peptide;

wherein:

$J^2$ is an amine group.

29. The imaging agent of claim 1, wherein when $M^{IG}$ is at the amino terminus, it is selected from N-acylated groups —NH(C=O)$R^G$ wherein the acyl group is selected from acetyl, benzyloxycarbonyl or trifluoroacetyl.

\* \* \* \* \*

SEQUENCE LISTING

```
<160> NUMBER OF SEQ ID NOS: 7

<210> SEQ ID NO 1
<211> LENGTH: 17
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (1)..(13)
<220> FEATURE:
```

```
<221> NAME/KEY: VARIANT
<222> LOCATION: (2)..(2)
<223> OTHER INFORMATION: N, H or Y
<220> FEATURE:
<221> NAME/KEY: DISULFID
<222> LOCATION: (3)..(11)
<220> FEATURE:
<221> NAME/KEY: VARIANT
<222> LOCATION: (4)..(4)
<223> OTHER INFORMATION: G, S, T or N
<220> FEATURE:
<221> NAME/KEY: VARIANT
<222> LOCATION: (8)..(8)
<223> OTHER INFORMATION: T or R
<220> FEATURE:
<221> NAME/KEY: VARIANT
<222> LOCATION: (15)..(15)
<223> OTHER INFORMATION: A, D, E, G or S
<220> FEATURE:
<221> NAME/KEY: VARIANT
<222> LOCATION: (16)..(16)
<223> OTHER INFORMATION: S or T
<220> FEATURE:
<221> NAME/KEY: VARIANT
<222> LOCATION: (17)..(17)
<223> OTHER INFORMATION: D or E

<400> SEQUENCE: 1

Cys Xaa Cys Xaa Gly Pro Pro Xaa Phe Glu Cys Trp Cys Tyr Xaa Xaa
1               5                   10                  15

Xaa

<210> SEQ ID NO 2
<211> LENGTH: 18
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (2)..(14)
<220> FEATURE:
<221> NAME/KEY: VARIANT
<222> LOCATION: (3)..(3)
<223> OTHER INFORMATION: N, H OR Y
<220> FEATURE:
<221> NAME/KEY: DISULFID
<222> LOCATION: (4)..(12)
<220> FEATURE:
<221> NAME/KEY: VARIANT
<222> LOCATION: (5)..(5)
<223> OTHER INFORMATION: G, S, T or N
<220> FEATURE:
<221> NAME/KEY: VARIANT
<222> LOCATION: (9)..(9)
<223> OTHER INFORMATION: T or R
<220> FEATURE:
<221> NAME/KEY: VARIANT
<222> LOCATION: (16)..(16)
<223> OTHER INFORMATION: A, D, E, G or S
<220> FEATURE:
<221> NAME/KEY: VARIANT
<222> LOCATION: (17)..(17)
<223> OTHER INFORMATION: S or T
<220> FEATURE:
<221> NAME/KEY: VARIANT
<222> LOCATION: (18)..(18)
<223> OTHER INFORMATION: D or E

<400> SEQUENCE: 2

Ser Cys Xaa Cys Xaa Gly Pro Pro Xaa Phe Glu Cys Trp Cys Tyr Xaa
1               5                   10                  15

Xaa Xaa
```

```
<210> SEQ ID NO 3
<211> LENGTH: 22
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (4)..(16)
<220> FEATURE:
<221> NAME/KEY: VARIANT
<222> LOCATION: (5)..(5)
<223> OTHER INFORMATION: N, H or Y
<220> FEATURE:
<221> NAME/KEY: DISULFID
<222> LOCATION: (6)..(14)
<220> FEATURE:
<221> NAME/KEY: VARIANT
<222> LOCATION: (7)..(7)
<223> OTHER INFORMATION: G, S, T or N
<220> FEATURE:
<221> NAME/KEY: VARIANT
<222> LOCATION: (11)..(11)
<223> OTHER INFORMATION: T or R
<220> FEATURE:
<221> NAME/KEY: VARIANT
<222> LOCATION: (18)..(18)
<223> OTHER INFORMATION: A, D, E, G or S
<220> FEATURE:
<221> NAME/KEY: VARIANT
<222> LOCATION: (19)..(19)
<223> OTHER INFORMATION: S or T
<220> FEATURE:
<221> NAME/KEY: VARIANT
<222> LOCATION: (20)..(20)
<223> OTHER INFORMATION: D or E

<400> SEQUENCE: 3

Ala Gly Ser Cys Xaa Cys Xaa Gly Pro Pro Xaa Phe Glu Cys Trp Cys
1               5                   10                  15

Tyr Xaa Xaa Xaa Gly Thr
            20

<210> SEQ ID NO 4
<211> LENGTH: 4
<212> TYPE: PRT
<213> ORGANISM: Artificial
<220> FEATURE:
<223> OTHER INFORMATION: synthetic peptide

<400> SEQUENCE: 4

Gly Gly Gly Lys
1

<210> SEQ ID NO 5
<211> LENGTH: 4
<212> TYPE: PRT
<213> ORGANISM: Artificial
<220> FEATURE:
<223> OTHER INFORMATION: synthetic peptide

<400> SEQUENCE: 5

Gly Ser Gly Lys
1

<210> SEQ ID NO 6
<211> LENGTH: 5
<212> TYPE: PRT
<213> ORGANISM: Artificial
<220> FEATURE:
<223> OTHER INFORMATION: synthetic peptide

<400> SEQUENCE: 6
```

```
Gly Ser Gly Ser Lys
1               5

<210> SEQ ID NO 7
<211> LENGTH: 26
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (4)..(16)
<220> FEATURE:
<221> NAME/KEY: DISULFID
<222> LOCATION: (6)..(14)

<400> SEQUENCE: 7

Ala Gly Ser Cys Tyr Cys Ser Gly Pro Pro Arg Phe Glu Cys Trp Cys
1               5                   10                  15

Tyr Glu Thr Glu Gly Thr Gly Gly Lys
            20              25
```